(12) United States Patent
Schooler et al.

(10) Patent No.: US 12,056,741 B1
(45) Date of Patent: Aug. 6, 2024

(54) DIGITAL CONTENT MATCHING SYSTEM

(71) Applicant: vrtly, Inc., San Ramon, CA (US)

(72) Inventors: Joseph Schooler, Campbell, CA (US); Min Wang, San Ramon, CA (US); Vojin Kos, Danville, CA (US)

(73) Assignee: vrtly, Inc., San Ramon, CA (US)

( * ) Notice: Subject to any disclaimer, the term of this patent is extended or adjusted under 35 U.S.C. 154(b) by 0 days.

(21) Appl. No.: 18/208,832

(22) Filed: Jun. 12, 2023

(51) Int. Cl.
| | |
|---|---|
| *G06Q 30/00* | (2023.01) |
| *G06N 3/0475* | (2023.01) |
| *G06Q 30/0251* | (2023.01) |
| *G06Q 30/0273* | (2023.01) |
| *G16H 40/20* | (2018.01) |

(52) U.S. Cl.
CPC ....... *G06Q 30/0275* (2013.01); *G06N 3/0475* (2023.01); *G06Q 30/0254* (2013.01); *G16H 40/20* (2018.01)

(58) Field of Classification Search
CPC ........... G06Q 30/0275; G06Q 30/0254; G16H 40/20; G06N 3/0475
See application file for complete search history.

(56) References Cited

U.S. PATENT DOCUMENTS

| | | | | |
|---|---|---|---|---|
| 2004/0044574 A1* | 3/2004 | Cochran | ................ | G06Q 30/02 705/14.57 |
| 2007/0011050 A1* | 1/2007 | Klopf | ................. | G06Q 30/0272 705/14.46 |
| 2009/0012868 A1* | 1/2009 | DeAngelis | ............. | G06Q 40/04 705/37 |
| 2009/0144157 A1* | 6/2009 | Saracino | ................ | G06Q 30/02 726/4 |
| 2010/0257060 A1* | 10/2010 | Kountis | ................. | G06Q 30/08 705/26.1 |
| 2014/0337137 A1* | 11/2014 | Robertson | .......... | G06Q 30/0264 705/14.61 |

FOREIGN PATENT DOCUMENTS

KR          102135146 B1 *   7/2020   ........... G06F 16/903

OTHER PUBLICATIONS

Online Bidding Platform Fliphound Adds Three Marad Digital Billboards in Baton Rouge to its Portfolio of Outdoor Displays Business Wire [New York] Jul. 24, 2014. (Year: 2014).*

* cited by examiner

*Primary Examiner* — Robert M Pond
(74) *Attorney, Agent, or Firm* — Schwegman Lundberg & Woessner

(57) ABSTRACT

Described is a system for the placement of digital content items on a digital content item space for a point of care (POC) facility by identifying a display interface for a point of care (POC) facility, the display interface including a digital content item space to display a digital content item, identifying one or more digital content item providers for the digital content item space;
accessing a selection of the one or more digital content item providers, and identifying a set of digital content item providers for the digital content item space based on the selection. The system then causes display of the digital content item on the display interface based on the identified set of digital content item providers.

14 Claims, 9 Drawing Sheets

DIGITAL CONTENT MATCHING SYSTEM

BACKGROUND

Point-of-care (POC) digital content delivery technology is a growing field that focuses on delivering important content to physicians and patients in a physician's office. This technology utilizes digital displays, tablets, and other forms of digital user interfaces to deliver targeted messages to patients in a healthcare setting.

POC digital content delivery technology typically includes a number of technical components. At POC locations, digital displays are the primary delivery mechanism for POC advertising. These displays are typically mounted in waiting rooms, exam rooms, and other areas where patients spend time. The POC user interfaces can display a variety of content, including educational videos, product promotions, and other targeted messages.

On the server side, content management systems (CMS) are typically used to manage the content displayed on digital displays. CMS software allows advertisers to create and manage targeted messages and ensures that appropriate content is displayed to the right patient at the right time.

BRIEF DESCRIPTION OF THE SEVERAL VIEWS OF THE DRAWINGS

To easily identify the discussion of any particular element or act, the most significant digit or digits in a reference number refer to the figure number in which that element is first introduced.

DETAILED DESCRIPTION

Figure 1:
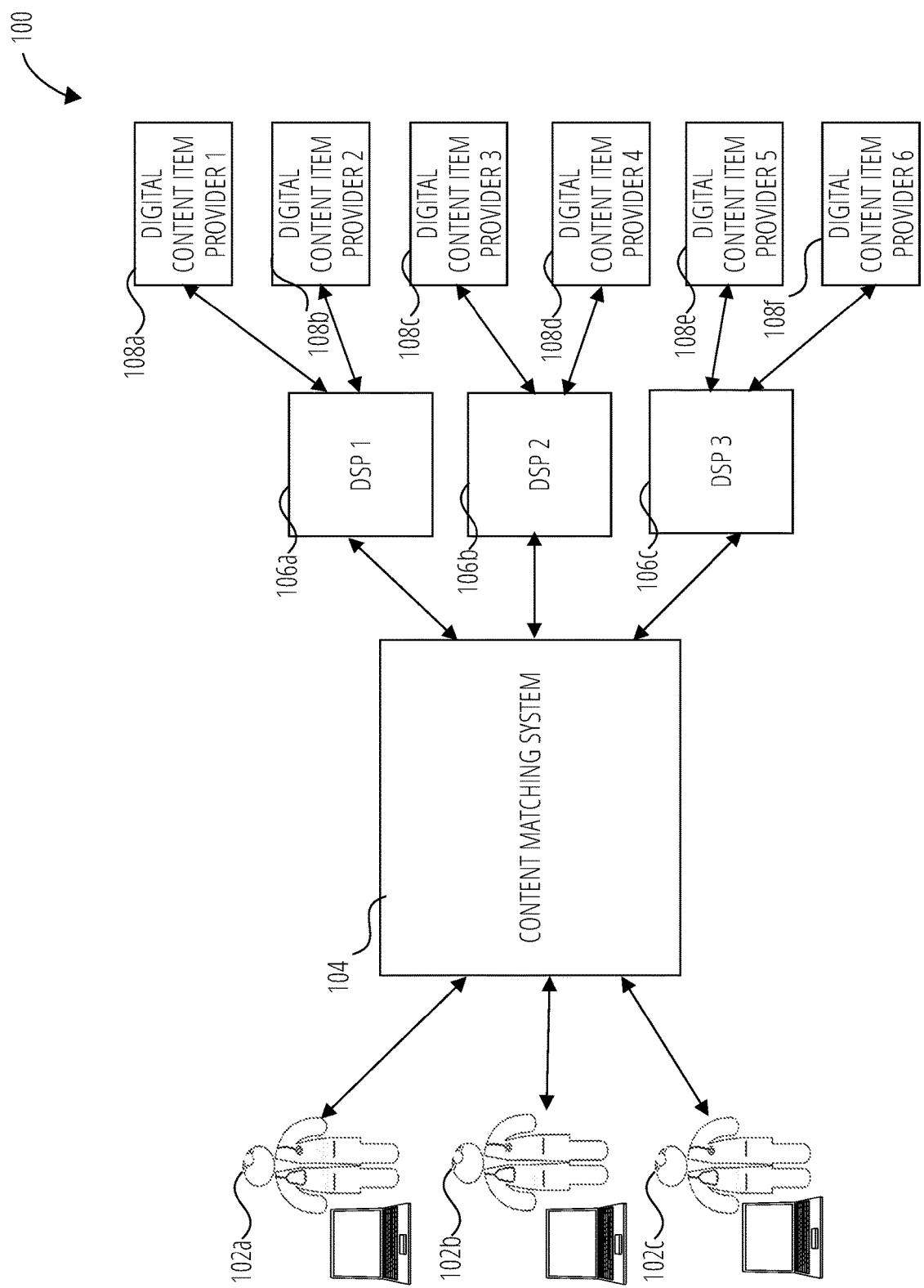
FIG. 1 is a block diagram that depicts an architecture for facilitating the sale of a digital content item space (e.g., inventory) on a POC's webpage, according to some examples.

Traditional programmatic advertising systems for point of care (POC) facilities (such as publishers) involve pre-determined digital content items being displayed on the available advertisement space without customization or control options for either the POC facility or the digital content item provider (such as brands or advertisers). This traditional approach has several pitfalls.

Traditional systems lack the ability to target specific audiences, leading to low engagement and wasted digital content item display spend. The digital content items may not be relevant to the specific audience or to the goals of the digital content item provider. POC facilities have limited control over the digital content items displayed on their screens, which can lead to irrelevant or inappropriate digital content items being shown to their patients or visitors. Moreover, digital content item providers are not able to customize their digital content items for specific POC locations or facilities, leading to generic and less effective advertising.

The innovative technology described herein addresses these pitfalls by allowing the POC facility to select which entities and corresponding goods/services they want to show on their available digital content item space. Moreover, digital content item providers are also able to select which POC facilities to show their available digital content items. POC facilities and digital content item providers can also narrow down the selection based on certain characteristics, such as a particular geographic location or characteristics of the POC facility's practice. This customization ensures that the digital content items are more relevant to the specific audience and more likely to generate engagement.

The content matching system uses a matrix to match digital content item spaces with digital content items based on the selections made by the digital content item providers and/or the POC facilities, which creates a more efficient process for a bid auction. This ensures that digital content item providers only pay for digital content item spaces that match their specific targeting criteria, and that POC facilities display digital content items from digital content item providers that also meet their specific criteria.

As such, the content matching system provides a two-way consent process between POC facilities and digital content item providers whereby mutual permission is needed from both the POC facility and the digital content item provider for digital content items to be displayed.

Overall, the technology improves on traditional systems by providing more control, customization, and efficiency for both the POC facility and the digital content item provider, resulting in more effective and efficient programmatic advertising.

Programmatic Advertising Solutions for POC Facility's Digital Content Inventory

Example systems described herein relate to POC hardware and software solutions that seek to match POC digital content item space inventory (e.g., an ad supply) with digital content item providers (e.g., advertisers) willing to purchase that space (e.g., ad demand). While these examples are discussed with reference to POC facilities, other examples may be deployed more broadly and in other environments within which programmatic advertising is deployed.

Programmatic advertising enables automated buying and selling of digital content item space inventory in real-time through an automated bidding system. This technology empowers brands or agencies to purchase advertisement impressions on publisher inventory (e.g., screens, sites or applications) through a sophisticated ecosystem. The programmatic advertising described herein leverages workflow automation and machine learning algorithms to deliver the most effective digital content items to audiences based on multiple signals.

Programmatic advertising may offer several advantages, including increased efficiency, targeted marketing reach, transparency, and real-time measurement and optimization. By using programmatic advertising, digital content item providers (such as marketers) can more efficiently target specific audiences, resulting in increased advertising effectiveness. Moreover, programmatic advertising offers transparency in digital content item placement and pricing, allowing digital content item providers to optimize their advertising budgets in real-time. Programmatic advertising may also enable real-time measurement and optimization of campaigns, allowing digital content item providers to adjust their strategies in real-time based on performance data.

A programmatic advertising ecosystem may comprise an interconnected network of entities and technologies that enable automated buying and selling of digital content item inventory in real-time. Digital content item providers include entities that purchase digital content item inventory for or on behalf of their brands or clients. Digital content item providers can use demand-side platforms (DSPs) to create and manage advertising campaigns and place bids on available ad inventory.

Publishers (such as POC facilities) are the entities that own and monetize digital content item inventory on their properties (e.g., billboards, screens, websites, apps, or other digital platforms). Publishers can use supply-side platforms (SSPs) to manage and monetize their digital content item inventory, including creating and managing deal identifiers. SSPs include software platforms that allow publishers to sell their digital content item inventory on digital content item exchanges. SSPs use data about the publisher's website traffic to determine which digital content items are most likely to be clicked on.

Digital content item exchanges (such as ad exchanges) are digital marketplaces where digital content item providers and publishers can buy and sell digital content item inventory in real-time. Digital content item exchanges act as intermediaries between SSPs and DSPs, facilitating the automated buying and selling of ad inventory.

Data management platforms (DMPs) collect and analyze vast amounts of data to help advertisers and publishers make more informed decisions about their campaigns. DMPs can provide insights into audience behavior, which can be used to optimize campaigns and target specific audiences more effectively.

Advertisement inventory matching technology may be used within programmatic advertising systems to match advertisers with available digital content item inventory, such as digital content item spaces on billboards, screens, websites, applications, or other digital platforms. The DMPs analyze the characteristics of the digital content item inventory and the target audience to identify the best match for a particular advertiser's campaign.

One way that digital content item inventory matching is facilitated is through the use of deal identifiers (deal ID). Deal IDs are unique identifiers assigned to advertising deals or campaigns that are used to track and manage digital content item inventory. The deal IDs include details such as the number of digital content item impressions available, targeting criteria, and pricing terms. Deal IDs can be utilized in programmatic advertising to automate the process of buying and selling digital content item inventory.

When a buyer submits a bid for digital content item inventory, the deal identifier is used to match the buyer's bid with the relevant seller and ensure that the terms of the deal are met. To this end, advertisement inventory matching technology may use real-time bidding (RTB) to facilitate the buying and selling of ad inventory. RTB includes an automated auction process where digital content item providers bid on available digital content item impressions in real-time. Advertisement inventory matching technology may also use DMPs to collect and analyze data about users to improve digital content item targeting.

SSPs and DSPs facilitate advertisement inventory matching. SSPs operate to manage and monetize publisher digital content item inventory. SSPs provide a set of tools that enable publishers to manage digital content item inventory, including the creation and management of deal IDs. SSPs also offer real-time updates of available digital content item inventory, which allow buyers to bid on inventory that matches their campaign requirements.

SSPs use advertisement inventory matching technology, including data analysis techniques such as machine learning algorithms and predictive analytics, to match the buyer's bid with the most appropriate seller in real-time. SSPs enable real-time bidding by creating a digital marketplace that allows digital content item providers to bid on available digital content item inventory. When a buyer places a bid, the SSP uses its advertisement inventory matching technology to match the bid with the most suitable seller. The deal identifier generated by the SSP is then communicated to Demand-Side Platforms (DSPs) to match their bids with the appropriate seller.

DSPs manage advertiser campaigns by providing tools to create and manage campaigns. Digital content item providers can set specific targeting criteria such as location, demographics, and interests, which the DSPs use to match the campaign with the most appropriate digital content item inventory. DSPs place real-time bids on digital content item inventory based on the criteria specified in the campaign. When a DSP places a bid, the DSP includes the deal ID generated by the SSP, which enables the SSP to match the bid with the appropriate seller in real-time. DSPs use machine learning algorithms and other data analysis techniques to analyze vast amounts of data and identify the most appropriate ad inventory for a specific campaign.

Architecture for Digital Content Item Bidding

FIG. 1 depicts an architecture 100 for facilitating the sale of a digital content item space (e.g., inventory) on a POC's webpage, according to some examples. Matching available inventory from publishers (e.g., POC facilities) to digital content items from digital content item providers, as well as compensation from the digital content item provider back to the POC facility is described herein.

In some examples, the architecture 100 includes physicians 102a, 102b, and 102c (collectively referred to herein as physicians 102), a content matching system 104, DSPs 106a, 106b, and 106c (collectively referred to herein as DSPs 106), and digital content providers 108a, 108b, 108c, 108d, 108e, 108f (collectively referred to herein as digital content providers 108).

A physician uses a computing device such as a desktop computer, laptop, tablet, or cell phone to provide information regarding a digital content item space (e.g., ad inventory on a POC's webpage or on-site display) available to place digital content items from digital content item providers.

In such an instance, a digital content item request ("ad request") may be generated by a physician 102 (or an associated publisher) and can be transmitted to the content matching system 104. The content matching system 104 then communicates with DSPs 106 to sell the digital content item inventory to a digital content item provider 108.

The physician 102 (or an associated publisher) generates a digital content item request for transmission to the content matching system 104. The digital content item request may include all or any portion of the information collected from or of the physician 102 (as described further herein) and/or the POC facility.

The content matching system 104 sells the digital content item space in an auction environment to participating buyers. In some examples, the content matching system 104 sends POC facility digital content item spaces and digital content item provider bids to an external auction system. In other examples, the content matching system 104 performs the bid auctioning internally.

In some examples, the content matching system 104 initiates an auction for a particular digital content item space. The auction remains open to the submission of bids from one or more digital content item providers 108 for a predetermined amount of time. For example, an auction may remain open to the submission of bids for 100 milliseconds or some other amount of time shorter or longer than 100 milliseconds.

After the auction has closed, a winning bidder may be determined. The price the winning bidder pays for the digital content item space may depend, at least in part, on the amount the winning bidder and/or other bidders bid at the auction.

After a winning bid has been selected, the content matching system 104 generates and transmits a confirmation message to the winning bidder. Where a DSP placed the bid within the content matching system 104, the confirmation message may first be received by the DSP and the DSP can send confirmation to the winning digital content item provider.

Payment for the placement of the digital content item can then be transmitted. In some examples, when the content matching system 104 transmits the confirmation message to the DSP 106, a financial account maintained by the DSP may be automatically debited for the appropriate amount. Alternatively, payment to the content matching system 104 for placement of the digital content item can be scheduled for some time in the future.

Matching Publishers and Digital Content Item Providers

Figure 2:
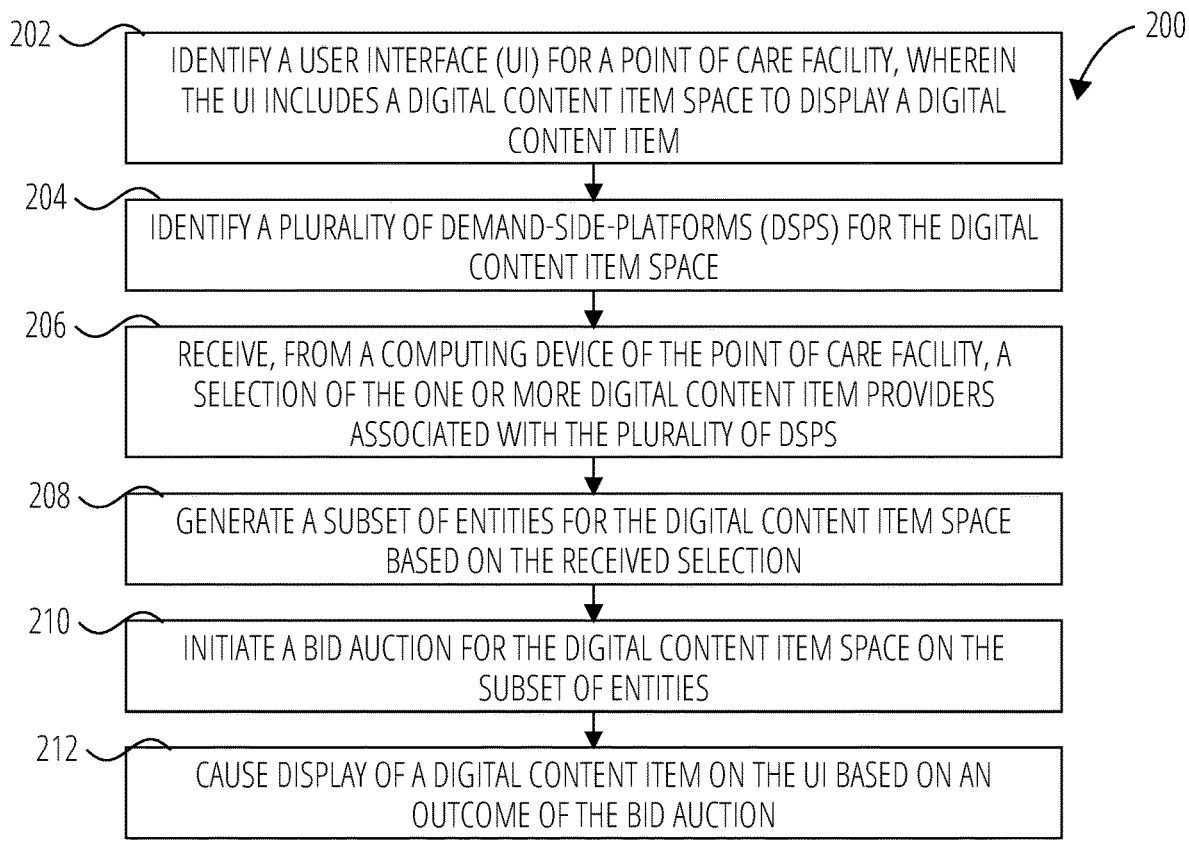
FIG. 2 is a flowchart that illustrates an example method for matching publishers and digital content item providers, according to some examples.

FIG. 2 illustrates an example method 200 for matching publishers and digital content item providers, according to some examples. Although the example method 200 depicts a particular sequence of operations, the sequence may be altered without departing from the scope of the present disclosure. For example, some of the operations depicted may be performed in parallel or in a different sequence that does not materially affect the function of the method 200. In other examples, different components of an example device or system that implements the method 200 may perform functions at substantially the same time or in a specific sequence.

At operation 202, the content matching system 104 identifies a display interface (such as a user interface (UI)) for a point of care facility. For the sake of simplicity, examples herein are described as a display interface and/or a user interface, but it is appreciated that either interface can be applied. The UI includes one or more digital content item spaces to display a digital content item from a digital content item provider (such as an advertisement from a company providing goods and services that are relevant for patients and physicians).

To identify various UIs for POC facilities that are available for sale in programmatic advertising, the content matching system 104 gathers information about POC facilities' digital content item space (e.g., ad space) and its corresponding UIs. Individual POC facilities can set up their inventory in the programmatic advertising platform and identify the available digital content item space where digital content items (e.g., ads) can be displayed.

The content matching system 104 can map the available digital content item space to the corresponding UIs within the POC facility's system. In some examples, if a POC facility has waiting room screens, the content matching system 104 maps the digital content item space available on those screens to the waiting room UI.

The content matching system 104 classifies the available UIs into different categories based on their location, size, and any other relevant criteria. In some examples, waiting room screens are classified as a specific type of UI, while exam room screens are classified as another.

At operation 204, the content matching system 104 identifies a plurality of DSPs for the digital content item space. Digital content item providers set their targeting criteria, such as a specific POC facility or geographic location they want to target. The content matching system 104 identifies the DSPs that match the digital content item provider's targeting criteria and are interested in bidding on the available digital content item space in the POC facility.

At operation 206, the content matching system 104 receives, from a computing device of the point of care facility, a selection of the one or more digital content item providers associated with the plurality of DSPs. As part of the onboarding process for the POC facilities (such as publishers of the digital content items), the POC facilities provide basic information about their facility, such as the type of facility, location, and number and types of screens available for advertising.

The content matching system 104 displays a user interface for the POC facilities to select one or more digital content item providers. The digital content item providers have digital content items available for the digital content item spaces. These digital content item providers include specific brands, products, or services that the POC facility believes would be relevant to their audience.

When selecting which digital content items to run in their point of care (POC) facility, a POC facility may be interested in various characteristics of digital content item providers. The POC facility may be interested in digital content items that are relevant to their patients and visitors, such as digital content items for healthcare products or services that are related to the facility's specialty or demographic. The POC facility may be interested in digital content items from brands or providers with a positive reputation, as this can reflect well on the facility and improve patient satisfaction. As such, enabling the POC facility to select one or more digital content item providers enables control over the types of digital content items displayed at their facility.

At operation 208, the content matching system 104 generates a subset of entities for the digital content item space based on the received selection. Once the POC facility selects desired digital content item providers for their available advertisement space, the content matching system 104 narrows down digital content item providers who can bid on the digital content item space.

In some cases, the content matching system 104 further narrows down matches based on selections received from the digital content item providers. For example, digital content item providers can select certain POC facilities to send their digital content items to. This enables digital content item providers with control over where their digital content items are displayed.

The content matching system 104 can map the selections of the POC facilities by the digital content item providers and selection of the digital content item providers by the POC facilities to identify matches between the two. For example, the content matching system 104 can generate a matching matrix where one dimension is associated with selections from POC facilities and another dimension is associated with selections from digital content item providers. The matrix can be used to identify matches of selections between the POC facilities and the digital content item providers, whereby the matches are used to initiate display of digital content items from these digital content item providers to the digital content item spaces of POC facilities (as further described herein).

In some cases, the digital content management system 104 further narrows down the match between digital content item providers and POC facilities. The content matching system 104 can use targeting criteria set by the POC facility to narrow down the pool of digital content item providers who can bid on the ad space. For example, if the POC facility has selected a particular medical product or service, the programmatic advertising platform can select only those advertisers whose campaigns are relevant to that product or service.

The content matching system 104 can narrow down the pool of digital content item providers based on the category of the digital content item provider. For example, if the POC facility has selected a particular pharmaceutical product, the programmatic advertising platform can select only those digital content item providers in the pharmaceutical industry or that sell that particular product or service.

The content matching system 104 can narrow down the pool of digital content item providers based on the reputation of the digital content item provider. For example, the platform can select only those digital content item providers who have a good track record of delivering high-quality digital content items and/or services and products, meeting the standards set by the POC facility.

The content matching system 104 can narrow down the pool of digital content item providers based on the budget of the digital content item provider. For example, the content matching system 104 can select only those digital content item providers who have the budget to compete for the digital content item space.

The content matching system 104 can narrow down the pool of digital content item providers based on their bidding history. For example, the content matching system 104 can select only those digital content item providers who have a good track record of bidding on similar ad spaces or campaigns.

In some cases, the content matching system 104 can use a combination of these factors to narrow down the pool of digital content item providers who can bid on the digital content item space, ensuring that the digital content items displayed in the POC facility are relevant and effective for their audience.

In some cases, the content matching system 104 further narrows the matched set based on factors of the POC facility. In some cases, the POC facility identifies the available digital content item space and provides specific information on the digital content item space itself. The POC facility can provide the physical location of the digital content item space within the POC facility, which can be important for digital content item providers to determine the best audience to target. The POC facility can provide information on the size of the screen or digital content item space where digital content items will be displayed, which can be important for digital content item providers to ensure that their ad creative fits and displays optimally. The POC facility provides technical requirements for the ad creative, such as file format or resolution, which can be provided to DSPs or advertisers to ensure that the ad is displayed correctly.

The POC facility can provide information about the audience demographics, such as age range or gender, that typically frequent their facility. This information can help digital content item providers to better target their digital content items to the desired audience. The POC facility can provide information on the duration of the digital content item space availability, such as the date range or number of times the digital content item will be displayed. This information can help digital content item providers to plan their campaigns effectively. The POC facility can provide information on any content restrictions or guidelines that advertisers must follow, such as restrictions on pharmaceutical digital content items.

The POC facility can provide information on where the digital content item space is located within the facility, such as in a waiting room or exam room, which can affect the effectiveness of the digital content item. Such information can include a waiting room, which includes a room (typically the first room) that patients and visitors enter when they arrive at a POC facility, an exam room is where patients meet with healthcare professionals for consultations, examinations, or treatments, a treatment room where patients receive medical treatments, such as IV therapies or injections, a procedure room where patients undergo medical procedures that require specialized equipment or facilities, such as minor surgeries, endoscopies, or biopsies, a laboratory where medical tests are performed on samples such as blood or urine, a radiology room is where imaging tests are performed, such as X-rays, CT scans, or MRIs, a staff room is where healthcare professionals can take a break, eat their meals, or complete paperwork, and/or the like.

At operation 210, the content matching system 104 initiates a bid auction for the digital content item space on the subset of digital content item providers. Once the subset of digital content item providers has been identified, the content matching system 104 initiates a real-time bidding process for the available digital content item space. The DSPs and/or the digital content item providers bid on the digital content item space based on targeting criteria and their own set budgets, with the highest bidder winning the auction.

At operation 212, the content matching system 104 causes display of a digital content item on the UI based on an outcome of the bid auction. Once the winning bid has been determined, the content matching system 104 can serve the digital content item from the winning digital content item provider to the available digital content item space in the POC facility.

There are several different types of digital content items that can be displayed in a point of care (POC) facility's digital content item space. The digital content item space includes static image digital content items, such as text, images, and a call-to-action. Digital content items can include a video, animation, or slideshow. Digital content items can include native ads that blend in with content around them, such as matching the look and feel of a user interface displaying information related to the POC facility and/or services provided. Digital content items can include elements that engage the viewer with interactive elements, or audio content such as a voiceover, which can be effective at reaching audiences who are not visually focused, such as patients in a waiting room.

Digital content item spaces in point of care (POC) facilities can include various types of screens and displays where digital content items can be displayed to patients or visitors.

Many POC facilities have screens in their waiting rooms that display information about the facility, health-related news, and advertisements. POC facilities can have screens in their exam rooms that can display educational content or advertisements. POC facilities can use digital signage, such as LED or LCD displays, to display ads in high-traffic areas such as lobbies, hallways, or elevators. In some cases, POC facilities provide in-room TVs for patients to use during their stay, which also display advertisements. POC facilities can provide mobile devices such as tablets or smartphones to patients or visitors, which can display digital content items.

The digital content item space can include audio advertisements that are played, such as audio played in a waiting room of a POC facility. The digital content item space can include ambient advertising that integrate digital content items into a surrounding environment, such as in elevator doors or on a wall of a POC facility. The digital content item space can display digital content items in an Extended Reality (XR) environment, such as on smartphones or Augmented Reality (AR) glasses, overlaying digital content on the user's view of the real world.

The digital content item space can include displays on wearable technology, such as on smartwatches or fitness trackers, reaching users through their personal devices while located at the POC facility. For example, the content matching system 104 can identify a geolocation of the user using personal devices of a user and identify that the user is located within the POC facility, which can initiate the matching and bidding process as described herein.

Example Matching of Publishers and Content Providers Using Matrix Matching

Figure 3:
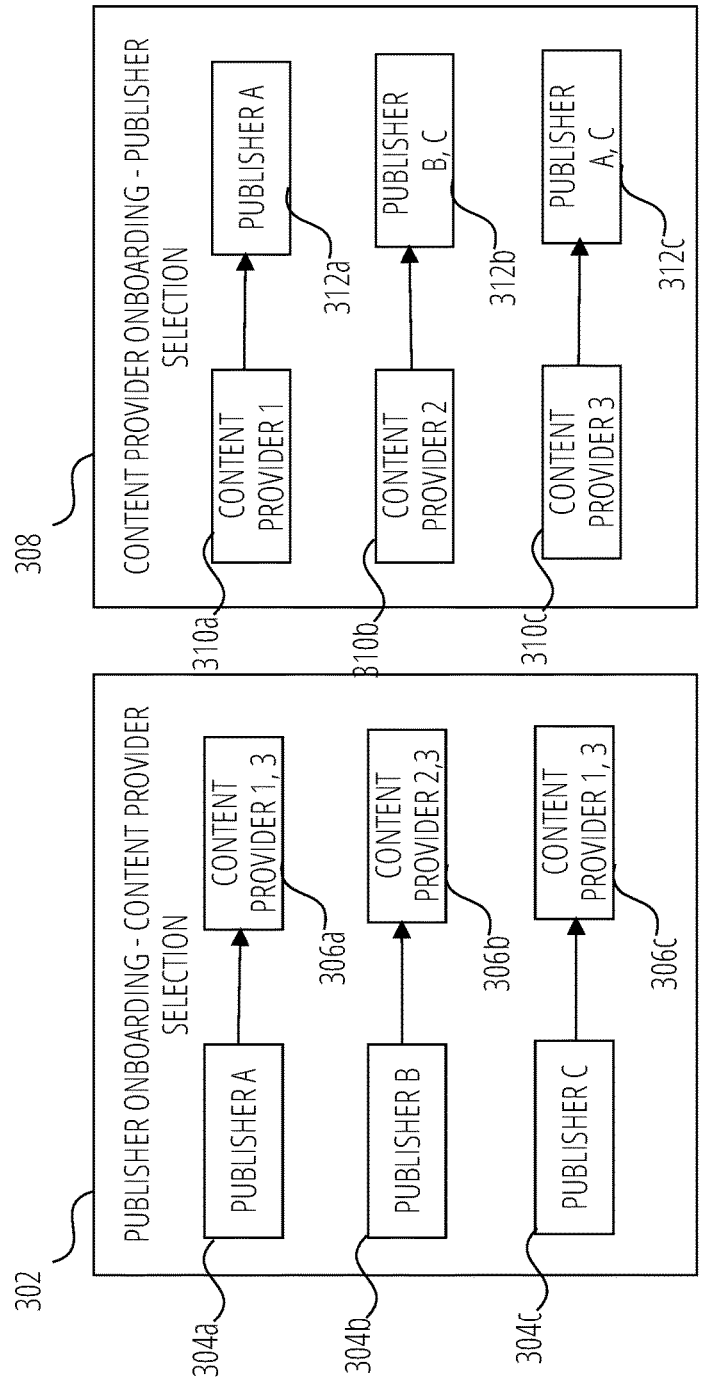
FIG. 3 is a block diagram that illustrates an onboarding process where publishers and digital content item providers make selections, according to some examples.

FIG. 3 illustrates an onboarding process 300 where publishers (such as POC facilities) and digital content item providers make selections, according to some examples. For the publisher onboarding process 302, the content matching system 104 of FIG. 1 causes display on a publisher user interface (such as on a physician's or POC facility's user interface) for the publisher to make selections of individual content providers. For example, publishers 304a, 304b, and 304c (collectively referred to herein as publishers 304) make selections, such as selections 306a, 306b, and 306c (collectively referred to herein as selections 306) of individual content providers.

In the example of FIG. 3, publisher 304a makes a selection 306a of content providers 1 and 3, publisher 304b makes a selection 306b of content providers 2 and 3, and publisher 304c makes a selection 306c of content providers 1 and 3.

For the content provider onboarding process 308, the content matching system 104 causes display on a content provider user interface (such as on a DSP's or advertiser's user interface) for the content provider to make selections of individual publishers. For example, content providers 310a, 310b, and 310c (collectively referred to herein as content providers 310) make selections, such as selections 312a, 312b, and 312c (collectively referred to herein as selections 312) of individual publishers.

In the example of FIG. 3, content provider 310a makes a selection 312a of publisher A, content provider 310b makes a selection 312b of publisher B and C, and content provider 310c makes a selection 312c of publisher A and C.

In some cases, the content matching system 104 applies a machine learning model to automatically make or recommend selections. For example, a machine learning model can be trained to generate recommendations for a publisher to one or more content providers, and/or vice versa. The machine learning model can apply characteristics of the publisher and/or the content provider to make these recommendations (as further described herein).

Figure 4:
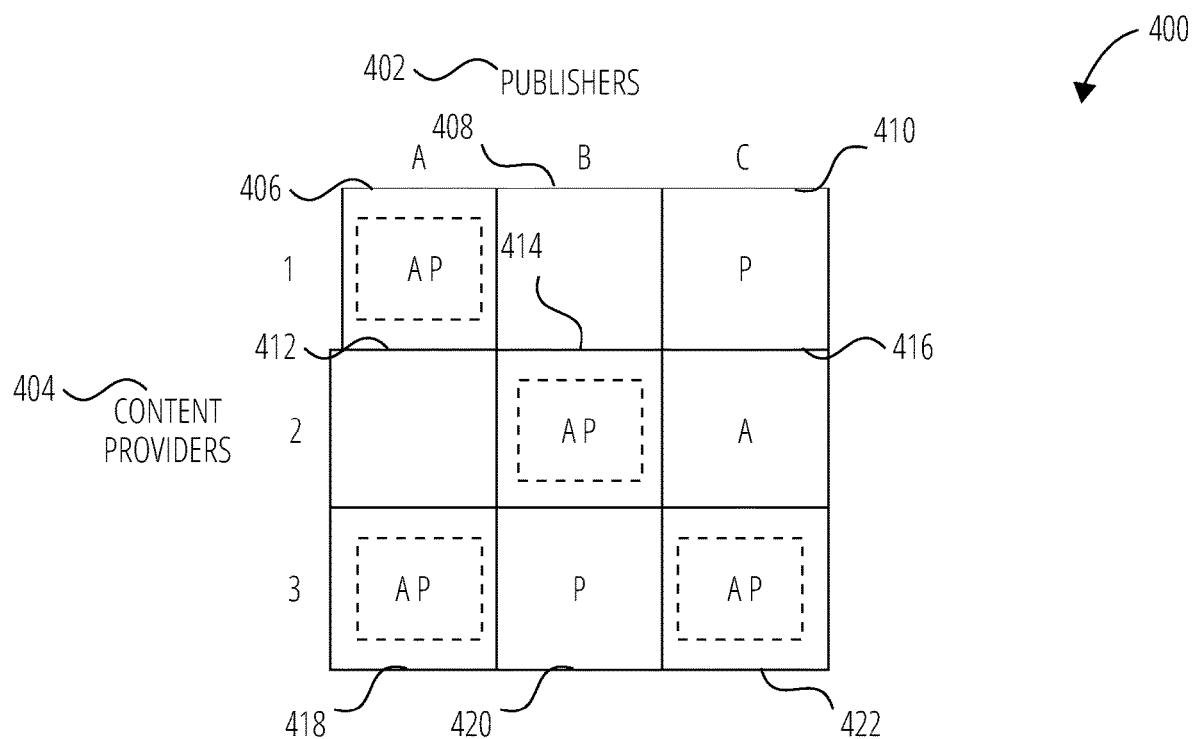
FIG. 4 is a drawing that illustrates an example of a matching matrix to match publishers with content providers based on selections, according to some examples.

FIG. 4 illustrates an example of a matching matrix 400 to match publishers with content providers based on selections made in FIG. 3, according to some examples. Publishers 402 are represented in one dimension and content providers 404 are represented in another dimension. As shown in FIG. 4, the selections of publishers made in FIG. 3 are shown in the matrix. Publisher A is shown to have selected content providers 1 and 3 in blocks 406 and 418, publisher B is shown to have selected content providers 2 and 3 in blocks 414 and 420, and publisher C is shown to have selected content providers 1 and 3 in blocks 410 and 422.

The selections of content providers made in FIG. 3 are also shown in the matrix. Content provider 1 is shown to have selected publisher A in block 406, content provider 2 is shown to have selected publisher B and C in block 414 and 416, and content provider 3 is shown to have selected publisher A and C in blocks 418 and 422. Blocks 408 and 412 are empty as no selections were made that correspond to these blocks.

The content matching system 104 applies the matrix 400 to identify matches in blocks 406, 414, 418, and 422. Blocks 410 and 420 are not considered matches because although the publishers have made selections for these blocks, the content providers have not made selections for these blocks. Block 410 is also not considered a match because although the content provider 2 has made a selection of publisher C, publisher C has not made a selection of content provider 2.

In some examples, the content matching system 104 can match POC facilities with digital content item providers using their individual selections in other ways, apart from using a matching matrix. The content matching system 104 can represent POC facilities and digital content item providers as nodes in a graph, with edges connecting nodes indicating a match based on the selections. The content matching system 104 can then use graph algorithms to find an optimal set of matches between POC facilities and advertisers.

In some examples, the content matching system 104 can apply collaborative filtering techniques to predict matches between POC facilities and advertisers. By analyzing the selections and preferences of similar POC facilities or advertisers, the system can make recommendations for potential matches.

In some examples, the content matching system 104 can use genetic algorithms to evolve a population of potential matches between POC facilities and advertisers. The fitness function can be based on the selections and preferences of both parties. By iteratively applying selection, crossover, and mutation operations, the algorithm can converge towards a set of optimal matches.

In some examples, the content matching system 104 group POC facilities and advertisers into clusters based on their selections and preferences. Then, the content matching system 104 can perform matching within each cluster to increase the likelihood of finding compatible matches.

Bid Auctioning on Matches from the Matrix

Figure 5:
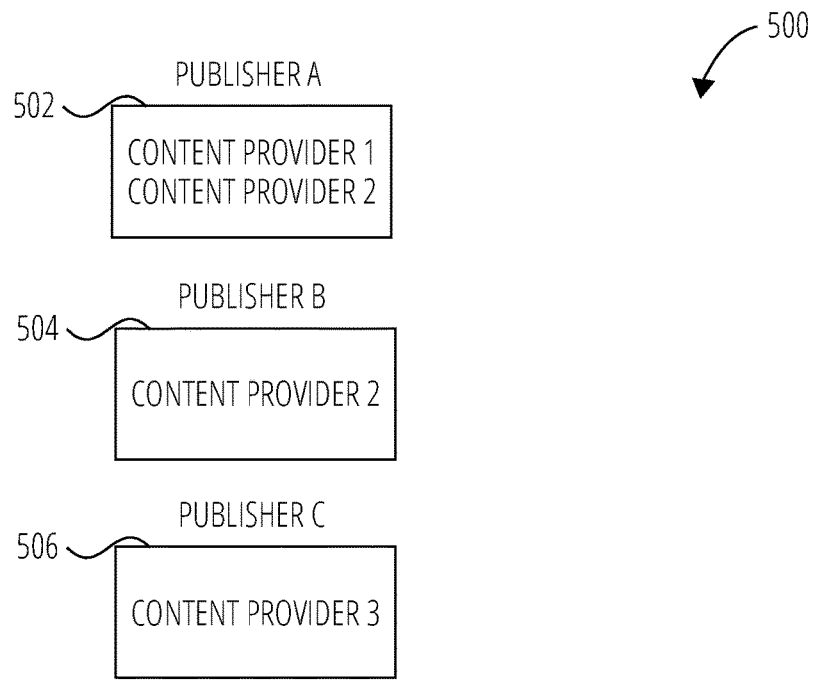
FIG. 5 is a block diagram that illustrates bid auctioning for certain matches found in the matching matrix, according to some examples.

FIG. 5 illustrates bid auctioning 500 for certain matches found in the matching matrix, according to some examples. From the matrix on FIG. 4, the content matching system 104 identifies that there are matches in blocks 406 and 418 for publisher A. Given that there are two matches, advertisements from content providers 1 and 2 can be displayed on a user interface 502 of publisher A.

The content matching system 104 of FIG. 1 identifies that there is only a single match in block 414 for publisher B. Advertisements from content provider 2 is displayed on a user interface 504 of publisher B. Likewise, the content matching system 104 identifies that there is only a single match in block 422 for publisher C. Advertisements from content provider 3 is displayed on a user interface 506 of publisher C.

In some examples, when there are more than a threshold number of matches (such as more than one match), the content matching system 104 can decide on which advertisements are to be displayed and/or when certain advertisements are to be displayed.

The content matching system 104 can hold an auction where the content providers bid for the digital content item space. The highest bidder wins the digital content item space, and their digital content item is displayed on the POC facility's display. The content matching system 104 can also apply real-time bidding to determine which digital content item should be shown to the user based on the highest bid at the time.

The content matching system 104 can use one or more machine learning algorithms to further match digital content item providers with POC facilities. For example, once matches have been found between the POC facilities and digital content item providers using matrix matching, the content matching system 104 applies a machine learning algorithm to assign digital content items to user interfaces of POC facilities, such as when there are multiple matches for a single POC facility.

The factors that the machine learning algorithm considers for determining which digital content items to display on digital content item spaces can be applied to other machine learning models described herein, and vice versa, such as the machine learning model to suggest or pre-select digital content item providers for POC facilities.

The machine learning algorithm can aggregate data of matched POC facilities and digital content item providers into a database, including the preferences of both parties, available digital content item spaces, characteristics of digital content items from the content providers, and/or the like.

The machine learning algorithm can determine which digital content item provider should be given preference for the available digital content item space based on the certain characteristics, such as characteristics of the digital content item provider and/or the POC facility.

The machine learning algorithm can decide which digital content item to place for the digital content item space based on one or more factors. For example, the machine learning algorithm can apply past engagement data to predict which digital content items that are likely to generate the highest engagement with the target audience. For example, the machine learning algorithm can predict that certain digital content items will perform better on certain devices or within certain locations within a POC facility.

The machine learning algorithm can use the data gathered to determine the most effective placement of each digital content item. This can include factors such as the size of the digital content item or the digital content item space, location on a webpage or user interface display, a device type that is configured to display the digital content item, and/or the like.

The algorithm can also use real-time data to optimize digital content item placement as the user interacts with the digital content item. Real-time data can refer to data that is collected and processed in real-time or near real-time, as opposed to historical data that is collected over a longer period of time. If the user is spending more time interacting with certain parts of the digital content item, or scrolling or viewing past other parts, the algorithm can use this data to adjust the placement of the digital content item or the type of digital content item displayed in real-time to improve engagement.

The machine learning algorithm can provide reporting and feedback to both the POC facilities and digital content item providers on the performance of their digital content items. This can include metrics such as click-through rate, engagement rate, and conversion rate. The content matching system 104 can use this information to improve content and ad targeting for future campaigns and/or to further retrain the machine learning model to be more effective with certain campaigns (such as for a particular POC facility or audience).

In some cases, the machine learning algorithm uses data related to the POC facility or the digital content item provider, such as a location to determine which digital content items to display. For example, a larger population of certain types of procedures, treatments, diseases, and/or the like may be more prevalent in a certain geographical area, resulting in the machine learning algorithm to weigh digital content from certain entities that provide relevant goods or services higher than others.

In some cases, the machine learning algorithm applies a temporal characteristic, such as the time of day, day of the week, day of the month, day of the year, season, holiday, and/or the like to determine which digital content items to display.

The machine learning model can consider the demographics and behaviors of the audience at a given POC facility. For example, the machine learning model can consider factors such as age, gender, location, and medical condition to determine which digital content items would be most effective.

The machine learning algorithm can consider the available digital content item space within a POC facility. For example, the machine learning model can determine which digital content items would be most effective based on the size, location, and format of the digital content item space. The size of the available digital content item space can impact the type of digital content item that is displayed. For example, if the digital content item is small, the machine learning algorithm can prioritize digital content items that are concise and to the point. On the other hand, if the digital content item space is larger, the algorithm can consider digital content items with more detailed messaging or visual content.

As for location, a digital content item space located near the entrance of a POC facility may be more effective for creating brand awareness, while a digital content item space located near a specific medical specialty may be more effective for targeting a specific audience. As for format, a machine learning algorithm can determine which types of digital content items are best suited for different formats, such as display or video digital content items.

In some cases, the machine learning algorithm can consider the preferences of digital content item providers, such as the type of digital content item they want to display or the target audience they want to reach. For example, if a digital content item provider is targeting a specific demographic, the algorithm can match that digital content item provider with POC facilities that have a high concentration of that demographic.

The machine learning algorithm can consider the budget of digital content item providers and/or estimated bids for a certain digital content item space. The machine learning algorithm can analyze the content and context of the digital content items, such as the language used, the images or videos included, and the context of the digital content item placement. This data can be used to match the digital content item with POC facilities that are relevant to the content and context.

The machine learning algorithm can consider a quality of the point of care facility. The machine learning algorithm can consider the patient volume at a given POC facility to determine the potential reach of digital content items displayed in that facility. Facilities with high patient volumes may be more attractive to digital content item providers as they offer a greater potential audience.

The location of a POC facility can also be a factor in assessing the quality of POC facilities. Facilities located in areas with higher population densities or in close proximity to medical facilities or other points of interest may be more attractive to advertisers.

The machine learning algorithm can also consider the quality of the health care providers at a given POC facility, such as their qualifications, experience, and patient satisfaction ratings. Facilities with high-quality health care providers may be more attractive to digital content item providers as they may be perceived as having greater credibility and trustworthiness.

The machine learning algorithm can consider factors related to patient engagement, such as patient satisfaction ratings, return visit rates, and online reviews. Facilities with high levels of patient engagement may be more attractive to digital content item providers as they may be perceived as having a more engaged and attentive audience.

The machine learning algorithm can consider a quality of the digital content item provider. The machine learning algorithm can consider the relevance of the goods and services provided by a digital content item provider to the audience of a specific POC facility. Digital content items that are more relevant to the audience may be more effective and receive higher engagement.

The machine learning algorithm can analyze the quality of the digital content item itself, such as the clarity of the messaging, the quality of the visual elements, and the overall appeal to the audience. The machine learning algorithm can consider the performance of the digital content item in other similar POC facilities or in other programmatic advertising campaigns. Digital content item providers that have a track record of producing effective ads may be preferred by the machine learning algorithm.

The machine learning algorithm can assess the reputation of the digital content item provider, such as their history of compliance with advertising regulations, their customer satisfaction ratings, and their online reviews. The machine learning algorithm can consider the budget of the digital content item provider, as well as their bidding history and average cost per click or view. Digital content item providers that have larger budgets or are willing to bid higher may be more attractive for the machine learning model.

The machine learning model can generate a composite score for the quality of a digital content item provider or a POC facility based on one or more factors described above. In some examples, the machine learning model adjusts the bidding characteristics based on such quality factors, such as applying a weighting to the bid.

The machine learning algorithm can be trained on data from point of care (POC) facilities and digital content item providers to match digital content items with available digital content item spaces, such as by using programmatic advertising.

The machine learning algorithm can be trained on the preferences of both digital content item providers and POC facilities, such as the types of digital content items they want to display or the target audience they want to reach. This data can be used to match specific digital content item providers with specific POC facilities based on their preferences.

The machine learning algorithm can be trained on user behavior and preferences, such as user engagement metrics, which can help the machine learning model to match digital content items with POC facilities that have patients who are most likely to engage with it, improving the chances of conversion.

The machine learning algorithm can be trained on advertisement performance metrics, such as click-through rate (if displayed on a selectable user interface), conversion rate, and engagement rate. This data can be used to identify which digital content items are the most effective at engaging users, and to match those digital content items with available ad spaces in POC facilities.

Systems and methods described herein include training a machine learning network, such as training to match digital content items from digital content item providers to digital content item spaces for POC facilities, or recommending digital content item providers to POC facilities (or vice versa). The machine learning algorithm can be trained using historical information that include historical digital content items, characteristics of the POC facilities and/or digital content item providers, and resulting metrics (such as matches, bidding characteristics, or engagement).

Training of models, such as artificial intelligence models, is necessarily rooted in computer technology, and improves modeling technology by using training data to train such models and thereafter applying the models to new inputs to make inferences on the new inputs. Here, the new inputs can be a new POC facility that begins onboarding with the system with an already existing database of digital content item providers. The trained machine learning model can determine which digital content items to provide to available digital content item spaces of the new POC facility.

Such training involves complex processing that typically requires a lot of processor computing and extended periods of time with large training data sets, which are typically performed by massive server systems. Training of models can require logistic regression and/or forward/backward propagating of training data that can include input data and expected output values that are used to adjust parameters of the models. Such training is the framework of machine learning algorithms that enable the models to be applied to new and unseen data (such as new POC facility data) and make predictions that the model was trained for based on the weights or scores that were adjusted during training. Such training of the machine learning models described herein reduces false positives and increases the performance of the matching of digital content items and spaces.

In some cases, the factors that the machine learning model can consider as described herein can instead be filters that a DSP, digital content item provider, and/or a POC facility can select. For example, a digital content item provider can filter types of POC facilities, the POC facility can filter digital content item providers that are in a certain geographical location, and/or the digital content item providers can apply a filter based on a composite score for the quality of the POC facility.

Onboarding Process for a POC Facility

Figure 6:
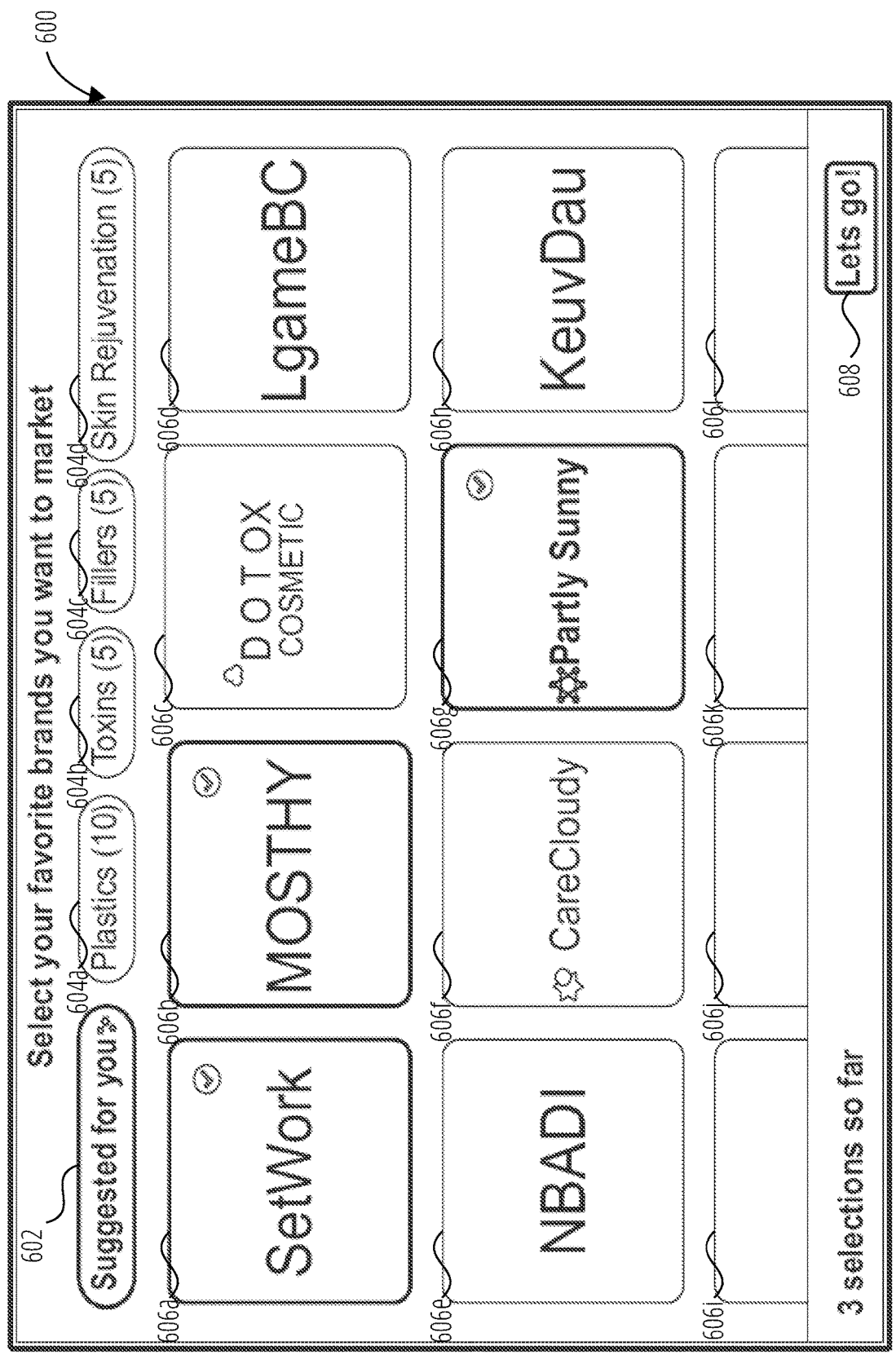
FIG. 6 is an illustration of a user interface of the onboarding process for a POC facility to select one or more digital content item providers, according to some examples.

FIG. 6 illustrates a user interface 600 of the onboarding process for a POC facility to select one or more digital content item providers, according to some examples. The content matching system 104 displays a listing of digital content item providers, such as digital content item providers 606a, 606b, 606c, 606d, 606e, 606f, 606g, 606h, 606i, 606j, 606k, 6061 (collectively referred to herein as digital content item providers 606). Each digital content item provider 606 is placed in individual user interface cells.

The content matching system 104 displays a selectable user interface element (e.g., a selectable icon representing the digital content item provider) within the user interface cell for individual digital content item providers. In some examples, the selectable user interface element is embedded in at least a portion of the user interface cell. For example, the selectable user interface element includes the entire cell for the digital content item provider 606a, such that the user can select anywhere in the user interface cell for the digital content item provider 606a to select the digital content item provider.

As shown in FIG. 6, digital content item providers 606a, 606b, and 606g have been selected by the user. In some cases, the content matching system 104 identifies suggested digital content item providers 606 to display and/or pre-selects certain digital content item providers 606 for the user. In some cases, the content matching system 104 provides an opt-in onboarding process where the user selects from a list of digital content item providers. In some cases, the content matching system 104 provides an opt-out onboarding process where the content matching system 104 pre-selects all or a subset of digital content item providers and enables the user to unselect from the list of digital content item providers.

The user can access such suggestions or pre-selections by selecting the "Suggested for you" user interface element 602. The user can also access other digital content item providers based on certain factors, such as categories plastic 604a, toxins 604d, fillers 604c, or skin rejuvenation 604b.

In some cases, a machine learning algorithm can be applied to suggest or pre-select digital content item providers 606 for the user. The content matching system 104 applies a machine learning algorithm to generate recommendations of digital content item providers for the POC facility to select from.

The machine learning algorithm for recommending digital content item providers can apply the data (as described further herein) for the machine learning algorithm for matching POC facilities with digital content item providers. For example, the machine learning algorithm for generating recommendations can base its recommendations or be trained on characteristics of the POC facility and/or individual digital content item providers, such as type of practice, type of goods/services, location, quality score, bidding history, demographics of the audience for the POC or the digital content provider, and/or the like.

The machine learning model for recommending digital content item providers to a POC facility can apply one or more factors considered by other machine learning models described herein (such as the machine learning model that matches digital content items with digital content item spaces). For example, the machine learning model for recommending digital content item providers can assesses the demographics and behaviors of the target audience at POC facilities, including factors such as age, gender, location, and medical condition, which enables the model to recommend digital content item providers that would be most effective in reaching the target audience.

In some cases, the model considers the available ad space within a POC facility, taking into account size, location, and format, which can help recommend suitable digital content item providers and digital content item types for each space, ensuring optimal ad performance. The model also can account for digital content item provider' preferences, such as the target audience or digital content item type they want to display, which ensures a match between the digital content item providers and POC facilities that share common objectives.

The model can factor in the budget of digital content item providers and the estimated bids for specific digital content item spaces, striking a balance between ad performance and cost-effectiveness. The quality of the POC facility is considered, including patient volume, location, healthcare provider quality, and patient engagement, here high-quality facilities may attract digital content item providers seeking greater credibility and an engaged audience.

Similarly, the model can evaluate the quality of the digital content item providers, considering factors such as relevance to the audience, digital content item quality, performance history, and reputation. Digital content item providers with a strong track record may be prioritized by the model when providing recommendations.

To generate recommendations, the machine learning model can use one or more of the factors described herein to generate a composite score for POC facilities and/or digital content item providers. This score can be used to rank potential matches and optimize the bidding process, taking into account both ad performance and quality factors.

By continuously updating its recommendations based on real-time data and feedback, the machine learning model ensures that POC facilities and digital content item providers benefit from the most effective and relevant digital content item placements. This dynamic approach enhances user engagement and optimizes advertising ROI for both parties.

In some examples, the content matching system 104 allows efficient use of the user interface, reducing the number of graphical user interfaces needed to initiate placement of digital content items on user displays to physicians or patients in the POC facility. In traditional digital content item display processes, a user of the POC facility does not even have the ability to make such selections of digital content item providers. Even if there was such a feature available in traditional systems, the POC facility would have to identify the goods and services provided by individual digital content item providers by visiting individual websites and assess relevance to goods or services provided by the POC facility. Moreover, the POC facility would have to locate the digital content item provider locations based on their website or a map website and determine if goods or services provided by the digital content item provider are in the area of the POC facility. Furthermore, the POC facility would have to vet digital content item providers by visiting review websites of these digital content item providers just to get a recommended list of digital content item providers.

Applying the machine learning algorithm, the content matching system 104 automatically generates highly relevant recommendations for the POC facility based on a variety of factors that the POC would like the machine learning model to consider, displaying the recommended digital content item providers in individual user interface cells for the user to select and initiate placement of digital content items in the digital content item spaces.

Moreover, the content matching system 104 enables users to quickly select digital content item providers on a single user interface and begin the digital content item placement onto digital content item spaces using a user selectable interface element 608 indicating that the user has completed the selection of digital content item providers based on selections of individual user interface cells. Such a selectable interface element 608 initiates the matching, bidding, and placement of the digital content items as described further herein.

Advantageously, the content matching system 104 according to some examples provides a practical solution to a technical problem of limited user interface real estate, complex navigation in a user interface, or both. The interaction system automatically identifies relevant digital content item providers using a machine learning model and displays options to select such digital content item providers using user interface cells. The user interface enables a user to directly select certain digital content item providers and to initiate the matching, bidding, and placement process. Moreover, given the limited user interface real estate with at least some current technology, the content matching system 104 may display an icon within the same cell of the digital content item provider or embed the selectable user interface element with at least a portion of the user interface cell. Thus, the technical problem of navigating through numerous graphical user interfaces may be solved by the practical solution of automatically identifying relevant digital content item providers, enabling a user to select digital content item providers in user interface cells, and applying digital content items onto digital content item spaces.

Hashing Customer Lists for Anonymity

Figure 7:
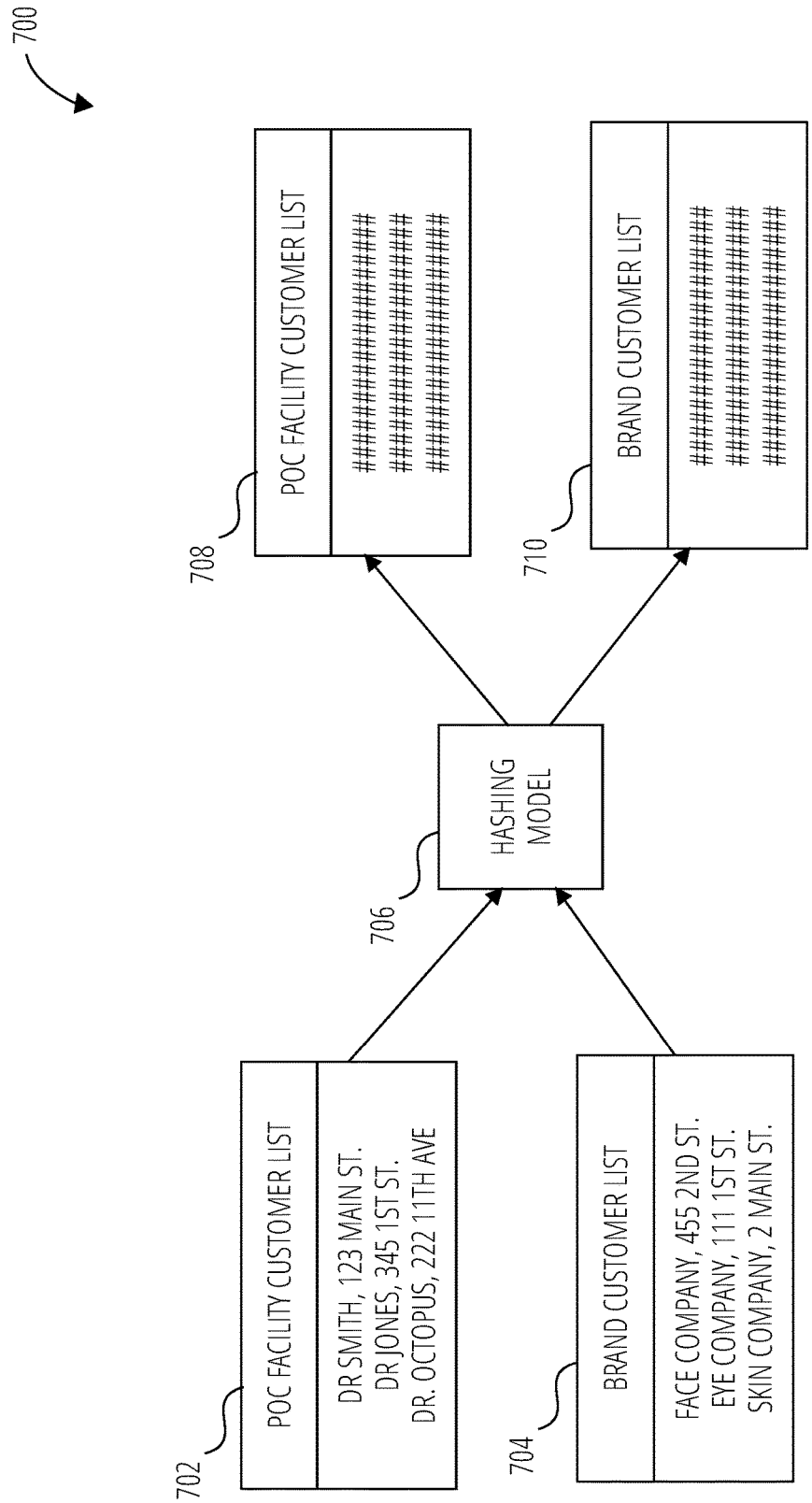
FIG. 7 is a block diagram that illustrates hashing of customer lists of POC facilities and brand customer lists, according to some examples.

FIG. 7 illustrates hashing 700 of POC facilities and brand customer lists, according to some examples. The content matching system 104 can hash information related to the POC facilities 702 and/or the brand customer list 704 using the hashing model 706. The content matching system 104 can hash protect sensitive information, such as customer lists, by converting the original data into a fixed-length string of characters using a cryptographic hash function. This process can be used to anonymize customer lists of Point-of-Care (POC) facilities and brand customer lists when matching between the two for sending digital content items from digital content item providers to user interface screens in POC facilities.

The content matching system 104 applies a cryptographic hash function to the customer lists, converting each individual data point (e.g., email address) into a unique fixed-length hash value. This hash value is a seemingly random string of characters that doesn't reveal any information about the original data. The same input can always produce the same hash value, but even a small change in the input can result in a completely different hash value.

The content matching system 104 can send the hashed customer list 708 of the POC facilities and the hashed customer list 710 of the digital content item providers to third parties, such as a third party that conducts the bid auction. In some cases, the customer lists are hashed by the POC facility and/or the digital content provider to the content matching system 104, such that the content matching system 104 does not have access to the customer lists. Since the data is hashed, the customer lists remain anonymous, and the third parties cannot derive the original customer information from the hash values.

In some cases, the content matching system 104 sends a subset of customer lists of POC facilities and/or available digital content item spaces from the POCs, and/or a subset of the customer lists of the digital content item providers and/or the digital content items to third parties. In some cases, the content matching system 104 receives a full customer list from the POC facilities and digital content item providers that are already hashed, and based on selections from the POC facilities and/or the digital content item providers, a subset of the hashed customer list is generated. The subset can be filtered based on one or more processes described herein, such as based on applying matrix matching to selections from the POC facility or digital content item providers.

The content matching system 104 and/or a third party bid auctioning system can compare the hashed customer lists of the POC facilities and the brands to identify matching hash values. When a match is found, the system indicates that the same customer appears on both lists. However, the system does not have access the original customer information, ensuring privacy.

Based on the matching results, digital content item providers can send targeted digital content items to the user interface screens of the POC facilities, knowing that there is a common customer base between them. By using hashing to anonymize customer lists, both POC facilities and brands can benefit from targeted advertising while maintaining the privacy and security of their customers' data.

In some examples, the hashing model described herein can be applied to information pertaining to the POC facility and/or the digital content item providers. For example, the hashing model can be applied to an email address, a physical address, a full legal name, or other characteristic that can be used to reveal the identify of the company.

System Architecture

Figure 8:
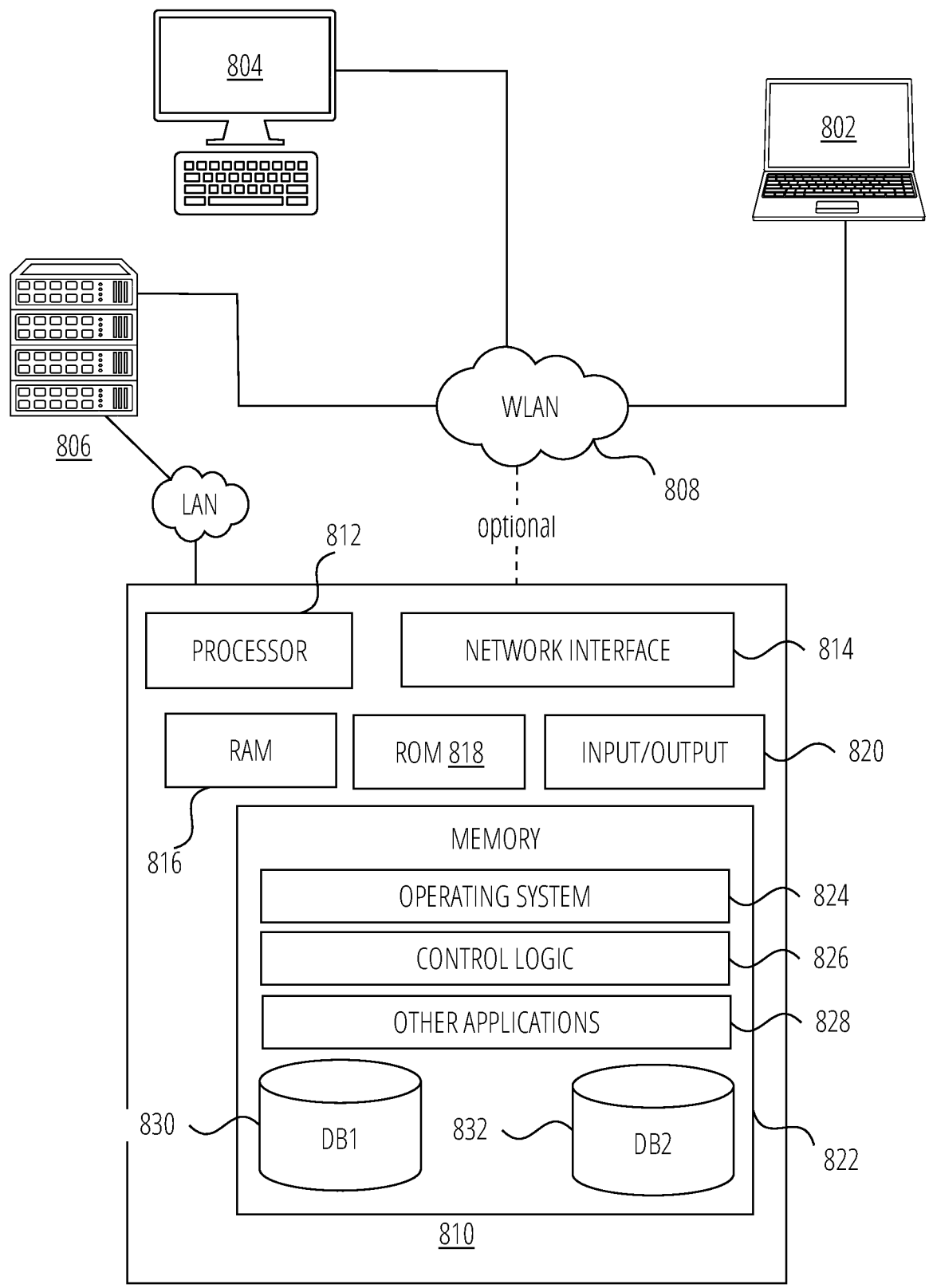
FIG. 8 illustrates a computer system architecture that may be used in accordance with one or more illustrative aspects described herein, according to some examples.

FIG. 8 illustrates one example of an AI system architecture and data processing device that may be used to implement one or more illustrative aspects described herein in a standalone and/or networked environment. Various network nodes, such as a data server 810, web server 806, computer 804, and laptop 802, may be interconnected via a wide area network 808 (WAN), such as the internet. Other networks may also or alternatively be used, including private intranets, corporate networks, LANs, metropolitan area networks (MANs) wireless networks, personal networks (PANs), and the like. Network 808 is for illustration purposes and may be replaced with fewer or additional computer networks. A local area network (LAN) may have one or more of any known LAN topology and may use one or more of a variety of different protocols, such as Ethernet. Devices, such as data server 810, web server 806, computer 804, laptop 802 and other devices (not shown), may be connected to one or more of the networks via twisted pair wires, coaxial cable, fiber optics, radio waves or other communication media.

The term "network" as used herein and depicted in the drawings refers not only to systems in which remote storage devices are coupled together via one or more communication paths, but also to stand-alone devices that may be coupled, from time to time, to such systems that have storage capability. Consequently, the term "network" includes not only a "physical network" but also a "content network," which is comprised of the data—attributable to a single entity—which resides across all physical networks.

The components may include data server 810, web server 806, client computer 804, and laptop 802. The data server 810 provides overall access, control and administration of databases and control software for performing one or more illustrative aspects described herein. The data server, such as data server 810, may be connected to web server 806 through which users interact with and obtain data as requested. Alternatively, data server 810 may act as a web server itself and be directly connected to the internet. The data server 810 may be connected to web server 806 through the network 808 (e.g., the internet), via direct or indirect connection, or via some other network. Users may interact with the data server 810 using remote computer 804 or laptop 802, e.g., using a web browser to connect to the data server 810 via one or more externally exposed web sites hosted by web server 806. The client computer 804 or laptop 802 may be used in concert with data server 810 to access data stored therein, or may be used for other purposes. For example, from client computer 804, a user may access web server 806 using an internet browser, as is known in the art, or by executing a software application that communicates with web server 806 and/or data server 810 over a computer network (such as the internet).

Servers and applications may be combined on the same physical machines, and retain separate virtual or logical addresses, or may reside on separate physical machines. FIG. 8 illustrates just one example of a network architecture that may be used, and those of skill in the art will appreciate that the specific network architecture and data processing devices used may vary, and are secondary to the functionality that they provide, as further described herein. For example, services provided by web server 806 and data server 810 may be combined on a single server.

Each component, such as the data server 810, web server 806, computer 804, or laptop 802, may be any type of known computer, server, or data processing device. Data server 810, e.g., may include a processor 812 controlling overall operation of the data server 810. The data server 810 may further include RAM 816, ROM 818, network interface 814, input/output interfaces 820 (e.g., keyboard, mouse, display, printer, etc.), and memory 822. The input/output interfaces 820 may include a variety of interface units and drives for reading, writing, displaying, and/or printing data or files. The memory 822 may further store operating system software 824 for controlling overall operation of the data server 810, control logic 826 for instructing the data server to perform aspects described herein, and other application software 828 providing secondary, support, and/or other functionality which may or may not be used in conjunction with aspects described herein. The control logic may also be referred to herein as the data server software or control logic 826. The functionality of the data server software may refer to operations or decisions made automatically based on rules coded into the control logic, made manually by a user providing input into the system, and/or a combination of automatic processing based on user input (e.g., queries, data updates, etc.).

The memory 822 may also store data used in performance of one or more aspects described herein, including a first database 832 and a second database 830. In some embodiments, the first database may include the second database (e.g., as a separate table, report, etc.). That is, the information can be stored in a single database, or separated into different logical, virtual, or physical databases, depending on system design. The web server 806, computer 804, or laptop 802 may have similar or different architecture as described with respect to data server 810. Those of skill in the art will appreciate that the functionality of data server 810 (or web server 806, computer 804, or laptop 802) as described herein may be spread across multiple data processing devices, for example, to distribute processing load across multiple computers, to segregate transactions based on geographic location, user access level, quality of service (QoS), etc.

One or more aspects may be embodied in computer-usable or readable data and/or computer-executable instructions, such as in one or more program modules, executed by one or more computers or other devices as described herein. Generally, program modules include routines, programs, objects, components, or data structures that perform particular tasks or implement particular abstract data types when executed by a processor in a computer or other device. The modules may be written in a source code programming language that is subsequently compiled for execution, or may be written in a scripting language such as (but not limited to) HTML or XML. The computer executable instructions may be stored on a computer readable medium such as a nonvolatile storage device. Any suitable computer readable storage media may be utilized, including hard disks, CD-ROMs, optical storage devices, magnetic storage devices, and/or any combination thereof. In addition, various transmission (non-storage) media representing data or events as described herein may be transferred between a source and a destination in the form of electromagnetic waves traveling through signal-conducting media such as metal wires, optical fibers, and/or wireless transmission media (e.g., air and/or space). Various aspects described herein may be embodied as a method, a data processing system, or a computer program product. Therefore, various functionalities may be embodied in whole or in part in software, firmware and/or hardware or hardware equivalents such as integrated circuits, field programmable gate arrays (FPGA), and the like. Particular data structures may be used to more effectively implement one or more aspects described herein, and such data structures are contemplated within the scope of computer executable instructions and computer-usable data described herein.

Machine-Learning Pipeline

Figure 9:
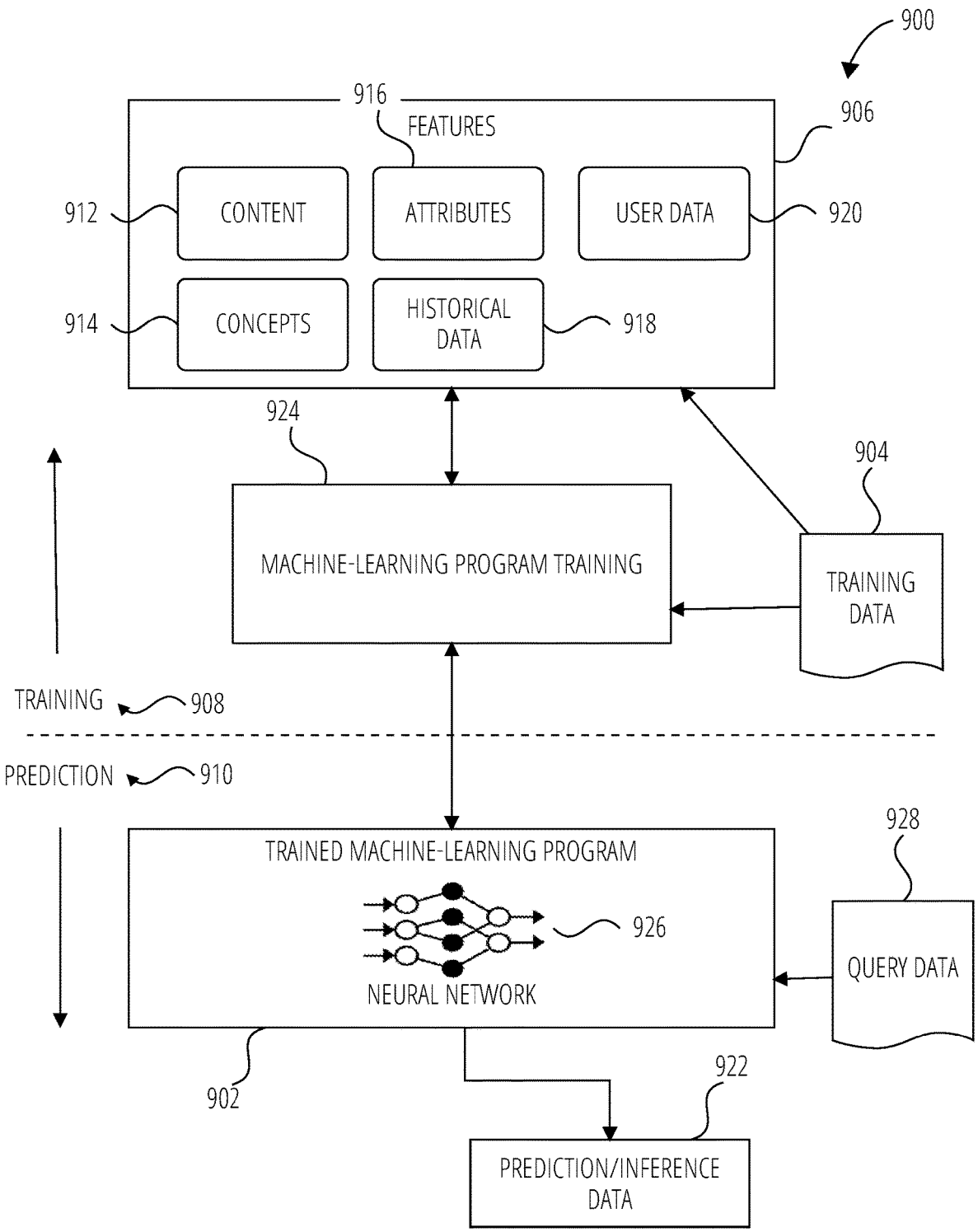
FIG. 9 illustrates training and use of a machine-learning program, according to some examples.

FIG. 9 is a flowchart depicting a machine-learning pipeline 900, according to some examples. The machine-learning pipelines 900 may be used to generate a trained model, for example the trained machine-learning program 902 of FIG. 9, described herein to perform operations associated with searches and query responses.

Overview

Broadly, machine learning may involve using computer algorithms to automatically learn patterns and relationships in data, potentially without the need for explicit programming to do so after the algorithm is trained. Examples of machine learning algorithms can be divided into three main categories: supervised learning, unsupervised learning, and reinforcement learning.

- Supervised learning involves training a model using labeled data to predict an output for new, unseen inputs. Examples of supervised learning algorithms include linear regression, decision trees, and neural networks.
- Unsupervised learning involves training a model on unlabeled data to find hidden patterns and relationships in the data. Examples of unsupervised learning algorithms include clustering, principal component analysis, and generative models like autoencoders.
- Reinforcement learning involves training a model to make decisions in a dynamic environment by receiving feedback in the form of rewards or penalties. Examples of reinforcement learning algorithms include Q-learning and policy gradient methods.

Examples of specific machine learning algorithms that may be deployed, according to some examples, include logistic regression, which is a type of supervised learning algorithm used for binary classification tasks. Logistic regression models the probability of a binary response variable based on one or more predictor variables. Another example type of machine learning algorithm is Naïve Bayes, which is another supervised learning algorithm used for classification tasks. Naïve Bayes is based on Bayes' theorem and assumes that the predictor variables are independent of each other. Random Forest is another type of supervised learning algorithm used for classification, regression, and other tasks. Random Forest builds a collection of decision trees and combines their outputs to make predictions. Further examples include neural networks which consist of interconnected layers of nodes (or neurons) that process information and make predictions based on the input data. Matrix factorization is another type of machine learning algorithm used for recommender systems and other tasks. Matrix factorization decomposes a matrix into two or more matrices to uncover hidden patterns or relationships in the data. Support Vector Machines (SVM) are a type of supervised learning algorithm used for classification, regression, and other tasks. SVM finds a hyperplane that separates the different classes in the data. Other types of machine learning algorithms include decision trees, k-nearest neighbors, clustering algorithms, and deep learning algorithms such as convolutional neural networks (CNN), recurrent neural networks (RNN), and transformer models. The choice of algorithm depends on the nature of the data, the complexity of the problem, and the performance requirements of the application.

The performance of machine learning models is typically evaluated on a separate test set of data that was not used during training to ensure that the model can generalize to new, unseen data. Evaluating the model on a separate test set helps to mitigate the risk of overfitting, a common issue in machine learning where a model learns to perform exceptionally well on the training data but fails to maintain that performance on data it hasn't encountered before. By using a test set, the system obtains a more reliable estimate of the model's real-world performance and its potential effectiveness when deployed in practical applications.

Although several specific examples of machine learning algorithms are discussed herein, the principles discussed herein can be applied to other machine learning algorithms as well. Deep learning algorithms such as convolutional neural networks, recurrent neural networks, and transformers, as well as more traditional machine learning algorithms like decision trees, random forests, and gradient boosting may be used in various machine learning applications.

Two example types of problems in machine learning are classification problems and regression problems. Classification problems, also referred to as categorization problems, aim at classifying items into one of several category values (for example, is this object an apple or an orange?). Regression algorithms aim at quantifying some items (for example, by providing a value that is a real number).

Figure 10:
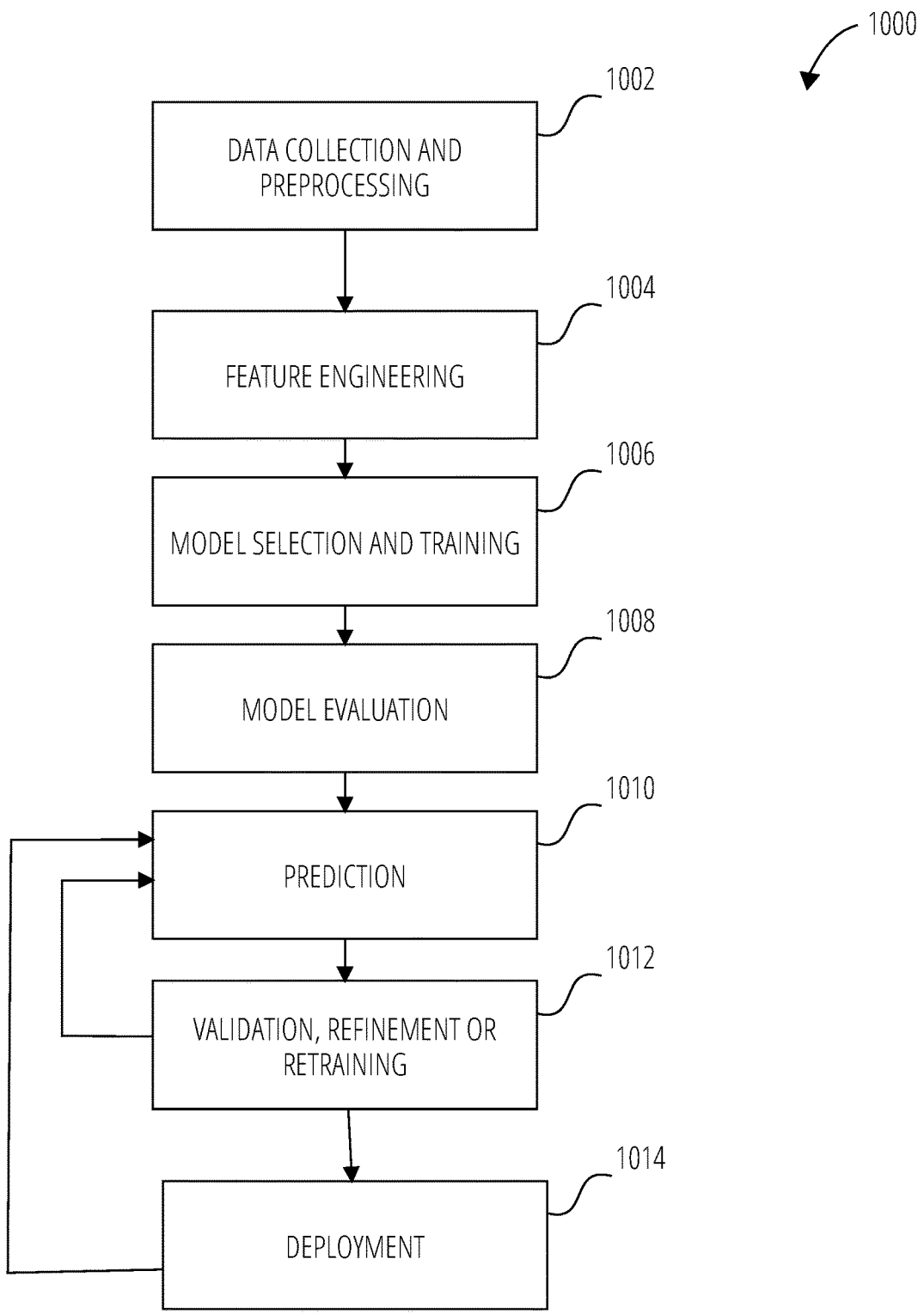
FIG. 10 illustrates a machine-learning pipeline, according to some examples.

Phases Generating a trained machine-learning program 902 may include multiple types of phases that form part of the machine-learning pipeline 900, including for example the following phases 1000 illustrated in FIG. 10:

Data collection and preprocessing 1002: This may include acquiring and cleaning data to ensure that it is suitable for use in the machine learning model. Data can be gathered from user content creation and labeled using a machine learning algorithm trained to label data. Data can be generated by applying a machine learning algorithm to identify or generate similar data. This may also include removing duplicates, handling missing values, and converting data into a suitable format.

Feature engineering 1004: This may include selecting and transforming the training data 904 to create features that are useful for predicting the target variable. Feature engineering may include (1) receiving features 906 (e.g., as structured or labeled data in supervised learning) and/or (2) identifying features 906 (e.g., unstructured or unlabeled data for unsupervised learning) in training data 904.

Model selection and training 1006: This may include specifying a particular problem or desired response from input data, selecting an appropriate machine learning algorithm, and training it on the preprocessed data. This may further involve splitting the data into training and testing sets, using cross-validation to evaluate the model, and tuning hyperparameters to improve performance. Model selection can be based on factors such as the type of data, problem complexity, computational resources, or desired performance.

Model evaluation 1008: This may include evaluating the performance of a trained model (e.g., the trained machine-learning program 902) on a separate testing dataset. This can help determine if the model is overfitting or underfitting and if it is suitable for deployment.

Prediction 1010: This involves using a trained model (e.g., trained machine-learning program 902) to generate predictions on new, unseen data.

Validation, refinement or retraining 1012: This may include updating a model based on feedback generated from the prediction phase, such as new data or user feedback.

Deployment 1014: This may include integrating the trained model (e.g., the trained machine-learning program 902) into a larger system or application, such as a web service, mobile app, or IoT device. This can involve setting up APIs, building a user interface, and ensuring that the model is scalable and can handle large volumes of data.

FIG. 9 illustrates two example phases, namely a training phase 908 (part of the model selection and trainings 1006) and a prediction phase 910 (part of prediction 1010). Prior to the training phase 908, feature engineering 1004 is used to identify features 906. This may include identifying informative, discriminating, and independent features for the effective operation of the trained machine-learning program 902 in pattern recognition, classification, and regression. In some examples, the training data 904 includes labeled data, which is known data for pre-identified features 906 and one or more outcomes.

Each of the features 906 may be a variable or attribute, such as individual measurable property of a process, article, system, or phenomenon represented by a data set (e.g., the training data 904). Features 906 may also be of different types, such as numeric features, strings, vectors, matrices, encodings, and graphs, and may include one or more of content 912, concepts 914, attributes 916, historical data 918 and/or user data 920, merely for example. Concept features can include abstract relationships or patterns in data. Content features include determining a context based on input information, such as determining a context of a user based on user interactions or surrounding environmental factors. Context features can include text features, such as frequency or preference of words or phrases, image features, such as pixels, textures, or pattern recognition, audio classification, such as spectrograms, and/or the like. Attribute features include intrinsic attributes (directly observable) or extrinsic features (derived), such as identifying square footage, location, or age of a real estate property identified in a camera feed. User data features include data pertaining to a particular individual or to a group of individuals, such as in a geographical location or that share demographic characteristics. User data can include demographic data (such as age, gender, location, or occupation), user behavior (such as browsing history, purchase history, conversion rates, click-through rates, or engagement metrics), or user preferences (such as preferences to certain video, text, or digital content items). Historical data includes past events or trends that can help identify patterns or relationships over time.

In training phases 908, the machine-learning pipeline 900 uses the training data 904 to find correlations among the features 906 that affect a predicted outcome or prediction/inference data 922.

With the training data 904 and the identified features 906, the trained machine-learning program 902 is trained during the training phase 908 during machine-learning program training 924. The machine-learning program training 924 appraises values of the features 906 as they correlate to the training data 904. The result of the training is the trained machine-learning program 902 (e.g., a trained or learned model).

Further, the training phase 908 may involve machine learning, in which the training data 904 is structured (e.g., labeled during preprocessing operations), and the trained machine-learning program 902 implements a relatively simple neural network 926 capable of performing, for example, classification and clustering operations. In other examples, the training phase 908 may involve deep learning, in which the training data 904 is unstructured, and the trained machine-learning program 902 implements a deep neural network 926 that is able to perform both feature extraction and classification/clustering operations.

A neural network 926 may, in some examples, be generated during the training phase 908, and implemented within the trained machine-learning program 902. The neural network 926 includes a hierarchical (e.g., layered) organization of neurons, with each layer including multiple neurons or nodes. Neurons in the input layer receive the input data, while neurons in the output layer produce the final output of the network. Between the input and output layers, there may be one or more hidden layers, each including multiple neurons.

Each neuron in the neural network 926 operationally computes a small function, such as an activation function that takes as input the weighted sum of the outputs of the neurons in the previous layer, as well as a bias term. The output of this function is then passed as input to the neurons in the next layer. If the output of the activation function exceeds a certain threshold, an output is communicated from that neuron (e.g., transmitting neuron) to a connected neuron (e.g., receiving neuron) in successive layers. The connections between neurons have associated weights, which define the influence of the input from a transmitting neuron to a receiving neuron. During the training phase, these weights are adjusted by the learning algorithm to optimize the performance of the network. Different types of neural networks may use different activation functions and learning algorithms, which can affect their performance on different tasks. Overall, the layered organization of neurons and the use of activation functions and weights enable neural networks to model complex relationships between inputs and outputs, and to generalize to new inputs that were not seen during training.

In some examples, the neural network 926 may also be one of a number of different types of neural networks or a combination thereof, such as a single-layer feed-forward network, a Multilayer Perceptron (MLP), an Artificial Neural Network (ANN), a Recurrent Neural Network (RNN), a Long Short-Term Memory Network (LSTM), a Bidirectional Neural Network, a symmetrically connected neural network, a Deep Belief Network (DBN), a Convolutional Neural Network (CNN), a Generative Adversarial Network (GAN), an Autoencoder Neural Network (AE), a Restricted Boltzmann Machine (RBM), a Hopfield Network, a Self-Organizing Map (SOM), a Radial Basis Function Network (RBFN), a Spiking Neural Network (SNN), a Liquid State Machine (LSM), an Echo State Network (ESN), a Neural Turing Machine (NTM), or a Transformer Network, merely for example.

In addition to the training phase 908, a validation phase may be performed evaluated on a separate dataset known as the validation dataset. The validation dataset is used to tune the hyperparameters of a model, such as the learning rate and the regularization parameter. The hyperparameters are adjusted to improve the performance of the model on the validation dataset.

The neural network 926 is iteratively trained by adjusting model parameters to minimize a specific loss function or maximize a certain objective. The system can continue to train the neural network 926 by adjusting parameters based on the output of the validation, refinement, or retraining block 1012, and rerun the prediction 1010 on new or already run training data. The system can employ optimization techniques for these adjustments such as gradient descent algorithms, momentum algorithms, Nesterov Accelerated Gradient (NAG) algorithm, and/or the like. The system can continue to iteratively train the neural network 926 even after deployment 1014 of the neural network 926. The neural network 926 can be continuously trained as new data emerges, such as based on user creation or system-generated training data.

Once a model is fully trained and validated, in a testing phase, the model may be tested on a new dataset that the model has not seen before. The testing dataset is used to evaluate the performance of the model and to ensure that the model has not overfit the training data.

In prediction phase 910, the trained machine-learning program 902 uses the features 906 for analyzing query data 928 to generate inferences, outcomes, or predictions, as examples of a prediction/inference data 922. For example, during prediction phase 910, the trained machine-learning program 902 is used to generate an output. Query data 928 is provided as an input to the trained machine-learning program 902, and the trained machine-learning program 902 generates the prediction/inference data 922 as output, responsive to receipt of the query data 928. Query data can include a prompt, such as a user entering a textual question or speaking a question audibly. In some cases, the system generates the query based on an interaction function occurring in the system, such as a user interacting with a virtual object, a user sending another user a question in a chat window, or an object detected in a camera feed.

In some examples the trained machine-learning program 902 may be a generative AI model. Generative AI is a term that may refer to any type of artificial intelligence that can create new content from training data 904. For example, generative AI can produce text, images, video, audio, code or synthetic data that are similar to the original data but not identical.

Some of the techniques that may be used in generative AI are:

Convolutional Neural Networks (CNNs): CNNs are commonly used for image recognition and computer vision tasks. They are designed to extract features from images by using filters or kernels that scan the input image and highlight important patterns. CNNs may be used in applications such as object detection, facial recognition, and autonomous driving.

Recurrent Neural Networks (RNNs): RNNs are designed for processing sequential data, such as speech, text, and time series data. They have feedback loops that allow them to capture temporal dependencies and remember past inputs. RNNs may be used in applications such as speech recognition, machine translation, and sentiment analysis Generative adversarial networks (GANs): These are models that consist of two neural networks: a generator and a discriminator. The generator tries to create realistic content that can fool the discriminator, while the discriminator tries to distinguish between real and fake content. The two networks compete with each other and improve over time. GANs may be used in applications such as image synthesis, video prediction, and style transfer.

Variational autoencoders (VAEs): These are models that encode input data into a latent space (a compressed representation) and then decode it back into output data. The latent space can be manipulated to generate new variations of the output data. They may use self-attention mechanisms to process input data, allowing them to handle long sequences of text and capture complex dependencies.

Transformer models: These are models that use attention mechanisms to learn the relationships between different parts of input data (such as words or pixels) and generate output data based on these relationships. Transformer models can handle sequential data such as text or speech as well as non-sequential data such as images or code.

In generative AI examples, the prediction/inference data 922 that is output include trend assessment and predictions, translations, summaries, image or video recognition and categorization, natural language processing, face recognition, user sentiment assessments, advertisement targeting and optimization, voice recognition, or media content generation, recommendation, and personalization.

EXAMPLES

In view of the above-described implementations of subject matter this application discloses the following list of examples, wherein one feature of an example in isolation or more than one feature of an example, taken in combination and, optionally, in combination with one or more features of one or more further examples are further examples also falling within the disclosure of this application.

Example 1 is a method comprising: identifying a display interface for a point of care (POC) facility, the display interface including a digital content item space to display a digital content item; identifying one or more digital content item providers for the digital content item space; accessing a selection of the one or more digital content item providers; identifying a set of digital content item providers for the digital content item space based on the selection; and causing display of the digital content item on the display interface based on the identified set of digital content item providers.

In Example 2, the subject matter of Example 1 includes, receiving, from the digital content item providers, a selection of POC facilities, the identifying of the set of digital content item providers being based on the selection of POC facilities from the digital content item providers.

In Example 3, the subject matter of Example 2 includes, determining that a first digital content item provider and a second digital content item provider are matched with the POC facility, and the causing of the display of the digital content item comprises causing display of a first digital content item from the first digital content item provider and a second digital content item from the second digital content item provider.

In Example 4, the subject matter of Examples 2-3 includes, determining that a first digital content item provider and a second digital content item provider is matched with the POC facility; and initiating a bid auction for the digital content item space between the first and second digital content item providers, wherein causing display of the digital content item on the display interface is further based on an outcome of the bid auction.

In Example 5, the subject matter of Example 4 includes, adjusting bid amounts by the first and second digital content item providers for the bid auction based on a characteristic of the POC facility.

In Example 6, the subject matter of Examples 4-5 includes, adjusting bid amounts by the first and second digital content item providers for the bid auction based on a characteristic of the corresponding digital content item provider.

In Example 7, the subject matter of Examples 4-6 includes, hashing of identifiable information of the digital content providers to generate hashed digital content provider identifiers; and hashing of identifiable information of the POC facility to generate a hashed POC facility identifier; wherein the bid auction is initiated using the hashed digital content provider identifiers and the hashed POC facility identifier.

In Example 8, the subject matter of Examples 2-7 includes, receiving, from POC facilities, a selection of the one or more digital content item providers; and identifying one or more matches between the selections from the POC facilities and from the digital content item providers, wherein the set of digital content item providers is generated with digital content item providers that are identified in the one or more matches for the POC facility.

In Example 9, the subject matter of Example 8 includes, generating a matrix of selections, wherein a first dimension of the matrix comprises the selections of the one or more digital content item providers from individual POC facilities and a second dimension of the matrix comprises the selections of the one or more POC facilities from individual digital content item providers, wherein identifying the one or more matches between the selections of the POC facilities and the digital content item providers is based on the generated matrix.

In Example 10, the subject matter of Examples 3-9 includes, receiving, from the one or more digital content item providers, a selection of one or more characteristics for POC facilities, wherein generating the set of digital content item providers is further based on the received selection of the one or more characteristics.

In Example 11, the subject matter of Example 10 includes, wherein the one or more characteristics include a quality score associated with the corresponding POC facility or a geographic location for the POC facility.

In Example 12, the subject matter of Examples 1-11 includes, applying the set of digital content item providers to a machine learning model to receive one or more recommended digital content item providers, wherein causing display of the digital content item includes causing display of one or more digital content items from the one or more recommended digital content item providers.

In Example 13, the subject matter of Example 12 includes, wherein the machine learning model is trained to identify recommended digital content item providers among the set of digital content item providers based on at least one of: a characteristic of a POC facility or a characteristic of the digital content item provider.

In Example 14, the subject matter of Examples 12-13 includes, training the machine learning model by: identifying training POC facility data, training digital content item provider data, and corresponding expected bid auctioning data; applying the training POC facility data and the training digital content item provider data to the machine learning model to receive output bid auctioning data; comparing the output bid auctioning data with the expected bid auctioning data to determine a loss parameter for the machine learning model; and updating a characteristic of the machine learning model based on the loss parameter.

In Example 15, the subject matter of Examples 1-14 includes, identifying the one or more digital content item providers by processing one or more characteristics of the POC facility using a machine learning model, wherein the machine learning model is trained to identify relevant digital content item providers based on the one or more characteristics of POC facilities.

In Example 16, the subject matter of Examples 1-15 includes, identifying the one or more digital content item providers by processing one or more characteristics of the one or more digital content item providers using a machine learning model, wherein the machine learning model is trained to identify relevant digital content item providers based on the one or more characteristics of digital content item providers.

In Example 17, the subject matter of Examples 1-16 includes, causing display of user interface cells corresponding to individual digital content item providers on a user interface for the POC facility.

In Example 18, the subject matter of Example 17 includes, wherein the display enables a user of the user interface to opt-in to digital content item providers by selecting at least a portion of the user interface cells corresponding to individual digital content item providers.

In Example 19, the subject matter of Examples 17-18 includes, wherein the display is initiated with the one or more digital content item providers preselected, and the display enables a user of the user interface to opt-out of digital content item providers by unselecting at least a portion of the user interface cells corresponding to individual digital content item providers.

Example 20 is a non-transitory computer-readable storage medium storing instructions that, when executed by at least one processor, cause the at least one processor to perform operations comprising: identifying a display interface for a point of care (POC) facility, the display interface including a digital content item space to display a digital content item; identifying one or more digital content item providers for the digital content item space; accessing a selection of the one or more digital content item providers; identifying a set of digital content item providers for the digital content item space based on the selection; and causing display of the digital content item on the display interface based on the identified set of digital content item providers.

Example 21 is a system comprising: at least one processor; and at least one memory component storing instructions that, when executed by the at least one processor, cause the at least one processor to perform operations comprising: identifying a display interface for a point of care (POC) facility, the display interface including a digital content item space to display a digital content item; identifying one or more digital content item providers for the digital content item space; accessing a selection of the one or more digital content item providers; identifying a set of digital content item providers for the digital content item space based on the selection; and causing display of the digital content item on the display interface based on the identified set of digital content item providers.

Example 22 is at least one machine-readable medium including instructions that, when executed by processing circuitry, cause the processing circuitry to perform operations to implement any of Examples 1-21.

Example 23 is an apparatus comprising means to implement any of Examples 1-21.

Example 24 is a system to implement any of Examples 1-21.

Example 25 is a method to implement any of Examples 1-21.

CONCLUSION

As used in this disclosure, phrases of the form "at least one of an A, a B, or a C," "at least one of A, B, or C," "at least one of A, B, and C," and the like, should be interpreted to select at least one from the group that comprises "A, B, and C." Unless explicitly stated otherwise in connection with a particular instance in this disclosure, this manner of phrasing does not mean "at least one of A, at least one of B, and at least one of C." As used in this disclosure, the example "at least one of an A, a B, or a C," would cover any of the following selections: {A}, {B}, {C}, {A, B}, {A, C}, {B, C}, and {A, B, C}.

Unless the context clearly requires otherwise, throughout the description and the claims, the words "comprise," "comprising," and the like are to be construed in an inclusive sense, as opposed to an exclusive or exhaustive sense, i.e., in the sense of "including, but not limited to." As used herein, the terms "connected," "coupled," or any variant thereof means any connection or coupling, either direct or indirect, between two or more elements; the coupling or connection between the elements can be physical, logical, or a combination thereof. Additionally, the words "herein," "above," "below," and words of similar import, when used in this application, refer to this application as a whole and not to any particular portions of this application. Where the context permits, words using the singular or plural number may also include the plural or singular number respectively. The word "or" in reference to a list of two or more items, covers all of the following interpretations of the word: any one of the items in the list, all of the items in the list, and any combination of the items in the list. Likewise, the term "and/or" in reference to a list of two or more items, covers all of the following interpretations of the word: any one of the items in the list, all of the items in the list, and any combination of the items in the list.

Although some examples, e.g., those depicted in the drawings, include a particular sequence of operations, the sequence may be altered without departing from the scope of the present disclosure. For example, some of the operations depicted may be performed in parallel or in a different sequence that does not materially affect the functions as described in the examples. In other examples, different components of an example device or system that implements an example method may perform functions at substantially the same time or in a specific sequence.

The various features, steps, and processes described herein may be used independently of one another, or may be combined in various ways. All possible combinations and subcombinations are intended to fall within the scope of this disclosure. In addition, certain method or process blocks may be omitted in some implementations.

What is claimed is:

1. A method comprising:
   receiving individual selections of point of care (POC) facilities from a plurality of digital content item providers;
   receiving individual selections of digital content item providers from POC facilities;
   generating a matrix matching digital content item providers with POC facilities, a first dimension of the matrix including digital content item providers, a second dimension of the matrix including POC facilities, individual cells of the matrix indicating whether a match between a particular POC facility and a particular digital content item provider is made;
   identifying a display interface for a first POC facility, the display interface including a digital content item space to display a digital content item;
   identifying one or more digital content item providers for the digital content item space by assessing matches of digital content item providers in the corresponding row or column of the matrix for the first POC facility;
   accessing a selection of the one or more digital content item providers;
   identifying a subset of digital content item providers for the digital content item space based on the selection;
   hashing of identifiable information of each digital content item provider of the subset of digital content item providers to generate individual hashed digital content provider identifiers;
   hashing of identifiable information of the POC facility to generate a hashed POC facility identifier;
   initiating a bid auction in real time for the digital content item space, the bid auction including bids submitted from the subset of digital content item providers, the initiating of the bid action resulting in a winning bid from a winning digital content item provider among the subset of digital content item providers, wherein initiating the bid auction to generate the winning bid includes performing the bid action using the hashed digital content provider identifiers and the hashed POC facility identifier to the bid auction and without using the unhashed digital content provider identifiers and the unhashed POC facility identifier; and
   automatically causing display in real time of the digital content item on the display interface of the digital content item space using a digital content item provided by the winning digital content item provider in response to the winning digital content item provider winning the bid auction.

2. The method of claim 1, further comprising: determining that a first digital content item provider and a second digital content item provider are matched with the POC facility, and the causing of the display of the digital content item comprises causing display of a first digital content item from the first digital content item provider and a second digital content item from the second digital content item provider.

3. The method of claim 2, further comprising receiving, from the one or more digital content item providers, a selection of one or more characteristics for POC facilities, wherein generating the set of digital content item providers is further based on the received selection of the one or more characteristics.

4. The method of claim 3, wherein the one or more characteristics include a quality score associated with the corresponding POC facility or a geographic location for the POC facility.

5. The method of claim 1, further comprising: adjusting bid amounts by first and second digital content item providers of the subset of digital content item providers for the bid auction based on a characteristic of the POC facility.

6. The method of claim 1, further comprising: adjusting bid amounts by first and second digital content item providers of the subset of digital content item providers for the bid auction based on a characteristic of the corresponding digital content item provider.

7. The method of claim 1, further comprising: causing display of user interface cells corresponding to individual digital content item providers on a user interface for the POC facility.

8. The method of claim 7, wherein the display enables a user of the user interface to opt-in to digital content item providers by selecting at least a portion of the user interface cells corresponding to individual digital content item providers.

9. The method of claim 7, wherein the display is initiated with the one or more digital content item providers preselected, and the display enables a user of the user interface to opt-out of digital content item providers by unselecting at least a portion of the user interface cells corresponding to individual digital content item providers.

10. The method of claim 1, further comprising:
    applying a characteristic of a particular POC facility to a machine learning model to receive from the machine learning model a list of recommended digital content item providers, wherein receiving of the individual selections of the POC facilities from the plurality of digital content item providers comprises:
    displaying the list of recommended digital content item providers to a computing device of the POC facility; and
    receiving a selection of digital content item providers from the list of recommended digital content item providers identified by the machine learning model by the POC facility.

11. The method of claim 10, further comprising:
    training the machine learning model to identify recommended digital content item providers based on one or more characteristics of POC facilities by:
    identifying training POC facility data, training digital content item provider data, and corresponding expected bid auctioning data;
    applying the training POC facility data and the training digital content item provider data to the machine learning model to receive output bid auctioning data;
    comparing the output bid auctioning data with the expected bid auctioning data to determine a loss parameter for the machine learning model; and
    updating a characteristic of the machine learning model based on the loss parameter.

12. The method of claim 1, further comprising:

applying a characteristic of a particular digital content item provider to a machine learning model to receive from the machine learning model a list of recommended POC facilities, wherein receiving the individual selections of the digital content item providers from the POC facilities comprises:

displaying the list of recommended POC facilities to a computing device of the digital content item provider; and receiving a selection of POC facilities from the list of recommended POC facilities identified by the machine learning model by the digital content item provider.

13. A non-transitory computer-readable storage medium storing instructions that, when executed by at least one processor, cause the at least one processor to perform operations comprising:

receiving individual selections of point of care (POC) facilities from a plurality of digital content item providers;

receiving individual selections of digital content item providers from POC facilities;

generating a matrix matching digital content item providers with POC facilities, a first dimension of the matrix including digital content item providers, a second dimension of the matrix including POC facilities, individual cells of the matrix indicating whether a match between a particular POC facility and a particular digital content item provider is made;

identifying a display interface for a first POC facility, the display interface including a digital content item space to display a digital content item;

identifying one or more digital content item providers for the digital content item space by assessing matches of digital content item providers in the corresponding row or column of the matrix for the first POC facility;

accessing a selection of the one or more digital content item providers;

identifying a subset of digital content item providers for the digital content item space based on the selection;

hashing of identifiable information of each digital content item provider of the subset of digital content item providers to generate individual hashed digital content provider identifiers;

hashing of identifiable information of the POC facility to generate a hashed POC facility identifier;

initiating a bid auction in real time for the digital content item space, the bid auction including bids submitted from the subset of digital content item providers, the initiating of the bid action resulting in a winning bid from a winning digital content item provider among the subset of digital content item providers, wherein initiating the bid auction to generate the winning bid includes performing the bid action using the hashed digital content provider identifiers and the hashed POC facility identifier to the bid auction and without using the unhashed digital content provider identifiers and the unhashed POC facility identifier; and automatically causing display in real time of the digital content item on the display interface of the digital content item space using a digital content item provided by the winning digital content item provider in response to the winning digital content item provider winning the bid auction.

14. A system comprising:

at least one processor; and at least one memory component storing instructions that, when executed by the at least one processor, cause the at least one processor to perform operations comprising:

receiving individual selections of point of care (POC) facilities from a plurality of digital content item providers;

receiving individual selections of digital content item providers from POC facilities;

generating a matrix matching digital content item providers with POC facilities, a first dimension of the matrix including digital content item providers, a second dimension of the matrix including POC facilities, individual cells of the matrix indicating whether a match between a particular POC facility and a particular digital content item provider is made;

identifying a display interface for a first POC facility, the display interface including a digital content item space to display a digital content item;

identifying one or more digital content item providers for the digital content item space by assessing matches of digital content item providers in the corresponding row or column of the matrix for the first POC facility;

accessing a selection of the one or more digital content item providers;

identifying a subset of digital content item providers for the digital content item space based on the selection;

hashing of identifiable information of each digital content item provider of the subset of digital content item providers to generate individual hashed digital content provider identifiers;

hashing of identifiable information of the POC facility to generate a hashed POC facility identifier;

initiating a bid auction in real time for the digital content item space, the bid auction including bids submitted from the subset of digital content item providers, the initiating of the bid action resulting in a winning bid from a winning digital content item provider among the subset of digital content item providers, wherein initiating the bid auction to generate the winning bid includes performing the bid action using the hashed digital content provider identifiers and the hashed POC facility identifier to the bid auction and without using the unhashed digital content provider identifiers and the unhashed POC facility identifier; and automatically causing display in real time of the digital content item on the display interface of the digital content item space using a digital content item provided by the winning digital content item provider in response to the winning digital content item provider winning the bid auction.

\* \* \* \* \*